(12) United States Patent
Gustafsson et al.

(10) Patent No.: US 9,913,983 B2
(45) Date of Patent: Mar. 13, 2018

(54) ALTERNATE STIMULATION STRATEGIES FOR PERCEPTION OF SPEECH

(71) Applicant: Cochlear Limited, Macquarie University, NSW (AU)

(72) Inventors: Johan Gustafsson, Göteborg (SE); Martin Hillbratt, Mölndal (SE); Kristian Åsnes, Mölndal (SE); Marcus Andersson, Gothenburg (SE)

(73) Assignee: Cochlear Limited, Macquarie University, NSW (AU)

( * ) Notice: Subject to any disclaimer, the term of this patent is extended or adjusted under 35 U.S.C. 154(b) by 553 days.

(21) Appl. No.: 14/063,420

(22) Filed: Oct. 25, 2013

(65) Prior Publication Data
US 2015/0119635 A1    Apr. 30, 2015

(51) Int. Cl.
*A61N 1/36* (2006.01)
*A61F 11/04* (2006.01)
*A61N 1/05* (2006.01)
*H04R 25/00* (2006.01)

(52) U.S. Cl.
CPC .......... *A61N 1/36032* (2013.01); *A61F 11/04* (2013.01); *A61F 11/045* (2013.01); *H04R 25/55* (2013.01); *H04R 25/606* (2013.01); *A61N 1/0541* (2013.01); *H04R 25/43* (2013.01); *H04R 2225/021* (2013.01); *H04R 2225/43* (2013.01); *H04R 2225/59* (2013.01); *H04R 2225/61* (2013.01)

(58) Field of Classification Search
CPC ......... H04R 25/00; H04R 25/70; A61F 11/00; A61F 11/04; A61M 2021/0022; A61M 2021/0027; A61N 1/36032
See application file for complete search history.

(56) References Cited

U.S. PATENT DOCUMENTS

| 4,581,491 A | 4/1986 | Boothroyd |
| 2009/0024183 A1 | 1/2009 | Fitchmun |
| 2009/0054980 A1* | 2/2009 | Ludlow .............. A61H 23/0245 623/9 |
| 2012/0245406 A1* | 9/2012 | Aghamohammadi .. A61F 11/04 600/25 |

* cited by examiner

*Primary Examiner* — Christine H Matthews
(74) *Attorney, Agent, or Firm* — Hauptman Ham, LLP; Martin J. Cosenza

(57) ABSTRACT

A system, including a first prosthetic device configured to evoke a hearing percept based on a first ambient sound and a second non-invasive device configured to stimulate skin based on a second ambient sound generated by a voice.

22 Claims, 14 Drawing Sheets

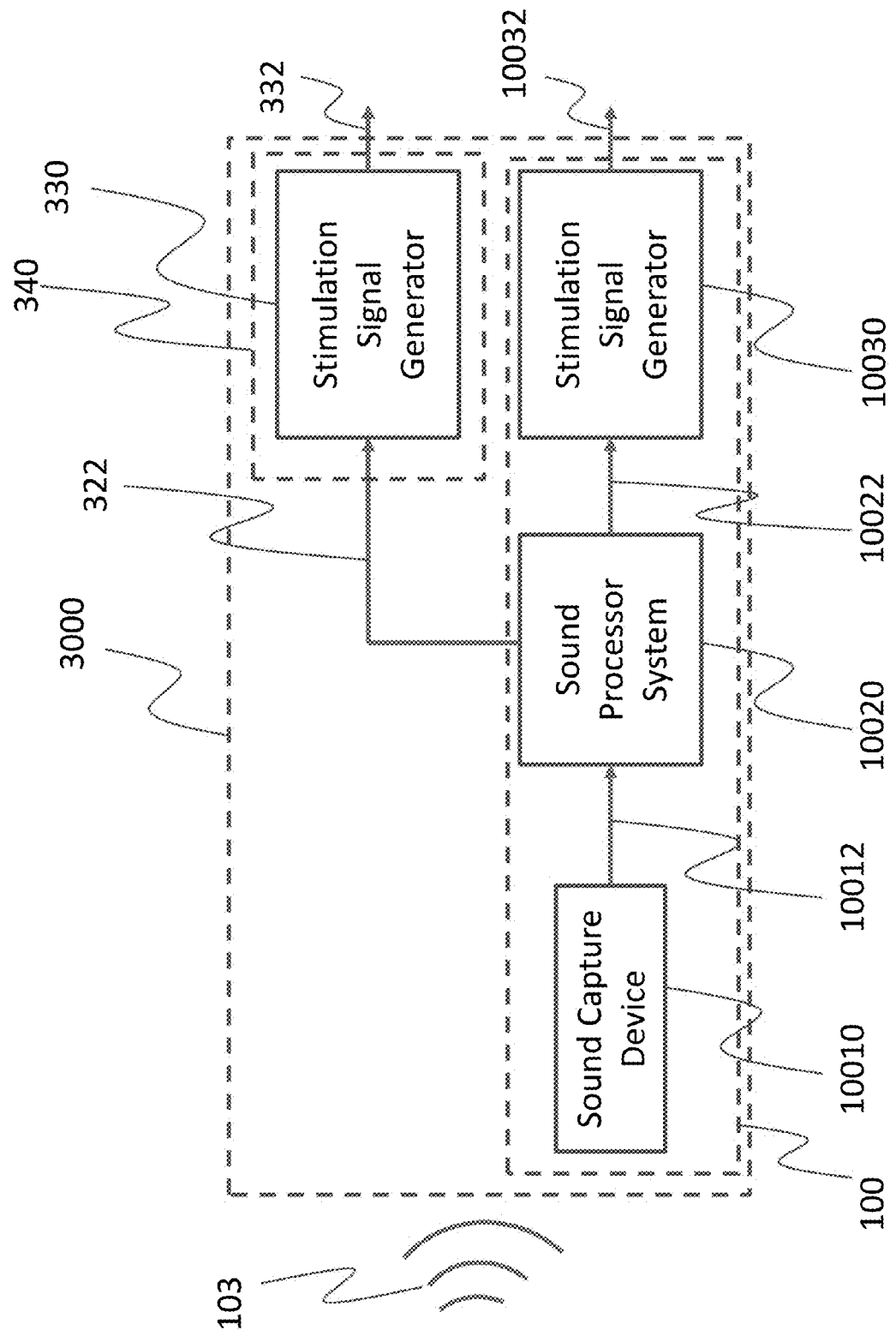

ALTERNATE STIMULATION STRATEGIES FOR PERCEPTION OF SPEECH

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as bone conduction devices, convert a received sound into vibrations. The vibrations are transferred through the skull to the cochlea causing generation of nerve impulses, which result in the perception of the received sound. In some instances, bone conduction devices can be used to treat single side deafness, where the bone conduction device is attached to the mastoid bone on the contra lateral side of the head from the functioning "ear" and transmission of the vibrations is transferred through the skull bone to the functioning ear. Bone conduction devices can be used, in some instances, to address pure conductive losses (faults on the pathway towards the cochlea) or mixed hearing losses (faults on the pathway in combination with moderate sensorineural hearing loss in the cochlea).

Another type of device that treats conductive hearing loss is a direct acoustic cochlear implant (DACI).

SUMMARY

In an exemplary embodiment, there is a system, comprising a first prosthetic device configured to evoke a hearing percept based on a first ambient sound and a second non-invasive device configured to stimulate skin based on a second ambient sound generated by a voice. In one example the second non-invasive device is configured to stimulate the skin when the voice is generated by a human, for example human speech. In further alternate embodiments the second stimulation device (i.e. second non-invasive device) is configured to provide stimulation if the voice is an animal voice, for example, the voice of a pet dog or cat.

In an exemplary embodiment, there is a system as detailed above and/or below, wherein the first device is a percutaneous bone conduction implant and the second device is a vibrator.

In an exemplary embodiment, there is a system as detailed above and/or below, wherein the first device is a passive transcutaneous bone conduction implant and the second device is a vibrator.

In an exemplary embodiment, there is a system as detailed above and/or below, wherein the first device is an active transcutaneous bone conduction implant, and the second device is a vibrator.

In an exemplary embodiment, there is a system as detailed above and/or below, wherein the first device is a middle ear implant and/or a Direct Acoustic Cochlear Implant (DACI), and the second device is a vibrator. In an exemplary embodiment, there is a system as detailed above and/or below, wherein the first device is an intra-oral bone conduction, and the second device is a vibrator.

In another exemplary embodiment, there is a system, comprising a hearing prosthesis configured to evoke a hearing precept based on a first captured sound, a hand-held electronic device in communication with the hearing prosthesis, wherein the hand-held electronic device is configured to stimulate skin based on the first captured sound.

In another exemplary embodiment, there is a method, comprising evoking a hearing percept in a recipient based on a first ambient sound and simultaneously evoking a tactile percept in the recipient based on a second ambient sound, wherein the evoked tactile percept does not evoke a hearing percept.

BRIEF DESCRIPTION OF THE DRAWINGS

Embodiments of the present invention are described below with reference to the attached drawings, in which:

FIG. 3C is another medium level exemplary functional diagraph of the exemplary embodiment of FIG. 3A:

DETAILED DESCRIPTION

Figure 1:
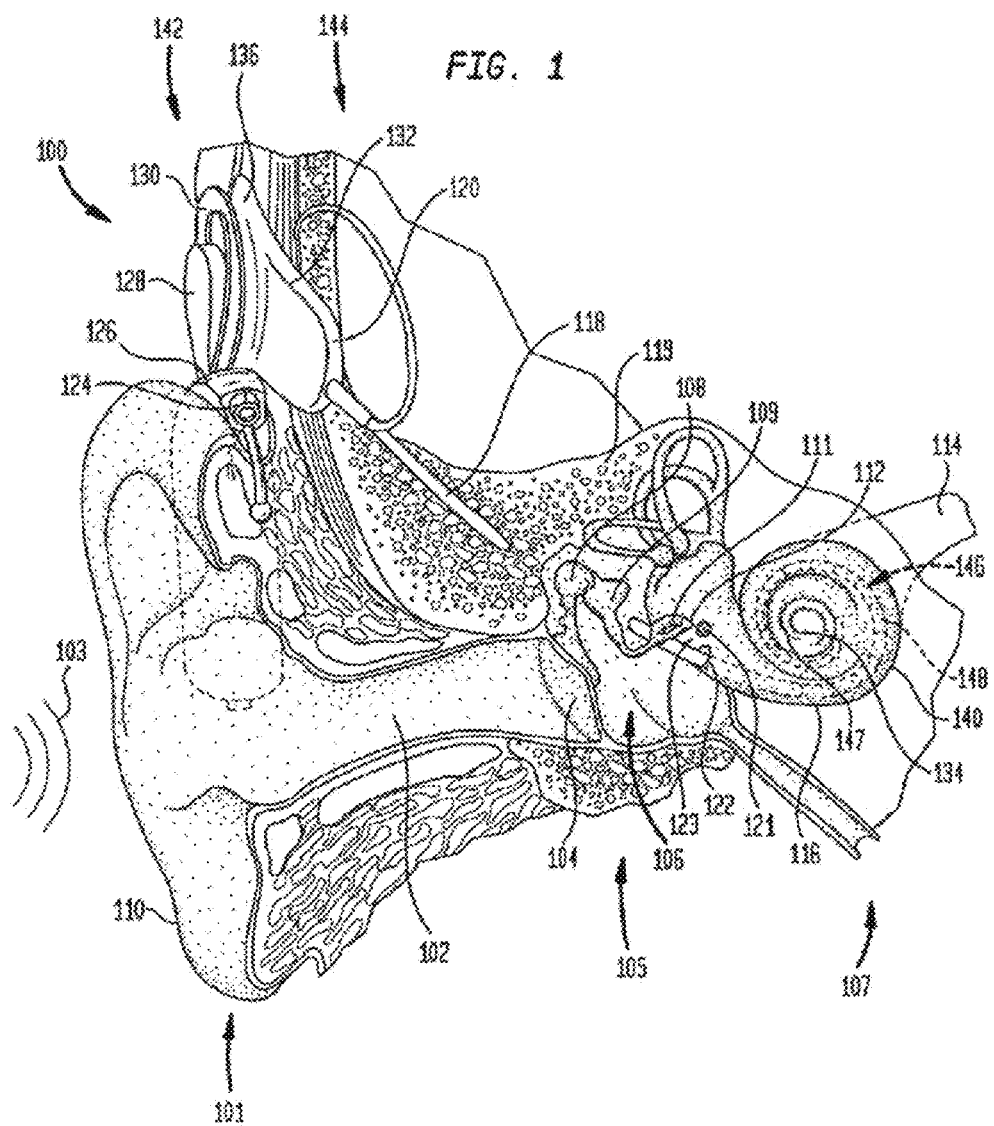
FIG. 1 is a perspective view of an exemplary hearing prosthesis utilized in some exemplary embodiments.

FIG. 1 is a perspective view of a cochlear implant 100, implanted in a recipient having an outer ear 101, a middle ear 105 and an inner ear 107. Components of outer ear 101, middle ear 105 and inner ear 107 are described below, followed by a description of cochlear implant system 100.

In a fully functional ear, outer ear 101 comprises an auricle 110 and an ear canal 102. An acoustic pressure or sound wave 103 is collected by auricle 110 and is channeled into and through ear canal 102. Disposed across the distal end of ear canal 102 is the tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external headpiece coil unit 128. External headpiece coil unit 128 comprises an external circular shaped coil 130 and, preferably, a magnet (not shown) secured directly or indirectly to external coil 130. Sound processing unit 126 processes the output of microphone 124 that is positioned, in the depicted embodiment, adjacent to the auricle 110 of the recipient. Sound processing unit 126 generates encoded signals, which are provided to the headpiece coil unit 128 via a cable (not shown).

Internal component 144 comprises internal receiver unit 132 including an implant coil 136, a stimulator unit 120, and an elongate electrode assembly 118. The internal receiver unit 132 may comprise a magnet (also not shown) fixed concentrically relative to the implant coil 136. The stimulator unit 120 is hermetically sealed within a biocompatible housing 132, sometimes collectively referred to as the implant unit. The implant coil 136 receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through the mastoid bone 119, and is implanted into cochlea 140. In some embodiments electrode assembly 118 may be implanted at least in basal region 116, and sometimes further. For example, electrode assembly 118 may extend towards apical end of cochlea 140, referred to as the cochlear apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises an electrode array 146 comprising a series of longitudinally aligned and distally extending electrodes 148, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

Because the cochlea is tonotopically mapped (that is, partitioned into regions each responsive to stimulus signals in a particular frequency range), each electrode of the implantable electrode array 146 delivers a stimulating signal to a particular region of the cochlea. In the conversion of sound to electrical stimulation, frequencies are allocated to individual electrodes of the electrode assembly that lie in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 126, that is, specific frequency bands with their associated signal processing paths, are mapped to a set of one or more electrodes to stimulate a desired nerve fiber or nerve region of the cochlea. Such sets of one or more electrodes for use in stimulation are referred to herein as "electrode channels" or "stimulation channels."

In cochlear implant 100, external coil 130 transmits electrical signals (i.e., power and stimulation data) to internal coil 136 via an inductive RF channel. Internal coil 136 is typically a closed loop wire antenna coil of multiple turns of electrically insulated single-strand/or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

Cochlear implant 100 can be used in a bimodal hearing prosthesis system, with the cochlear implant 100 fitted to one of the left or right ear, and another hearing prosthesis having a different principle of operation (e.g., an acoustic hearing aid) can be fitted to the other of the left or right ear. Alternatively, in a hybrid system, a cochlear implant and another hearing prosthesis having a different principle of operation can be fitted to one or both ears (the latter being a bilateral hybrid). With respect to a cochlear implant and another hearing prosthesis having a different principle of operation being fitted to one ear, a hearing prosthesis can be fitted to the other ear as well (a hearing prosthesis having a different principle of operation from a cochlear implant).

Figure 2:
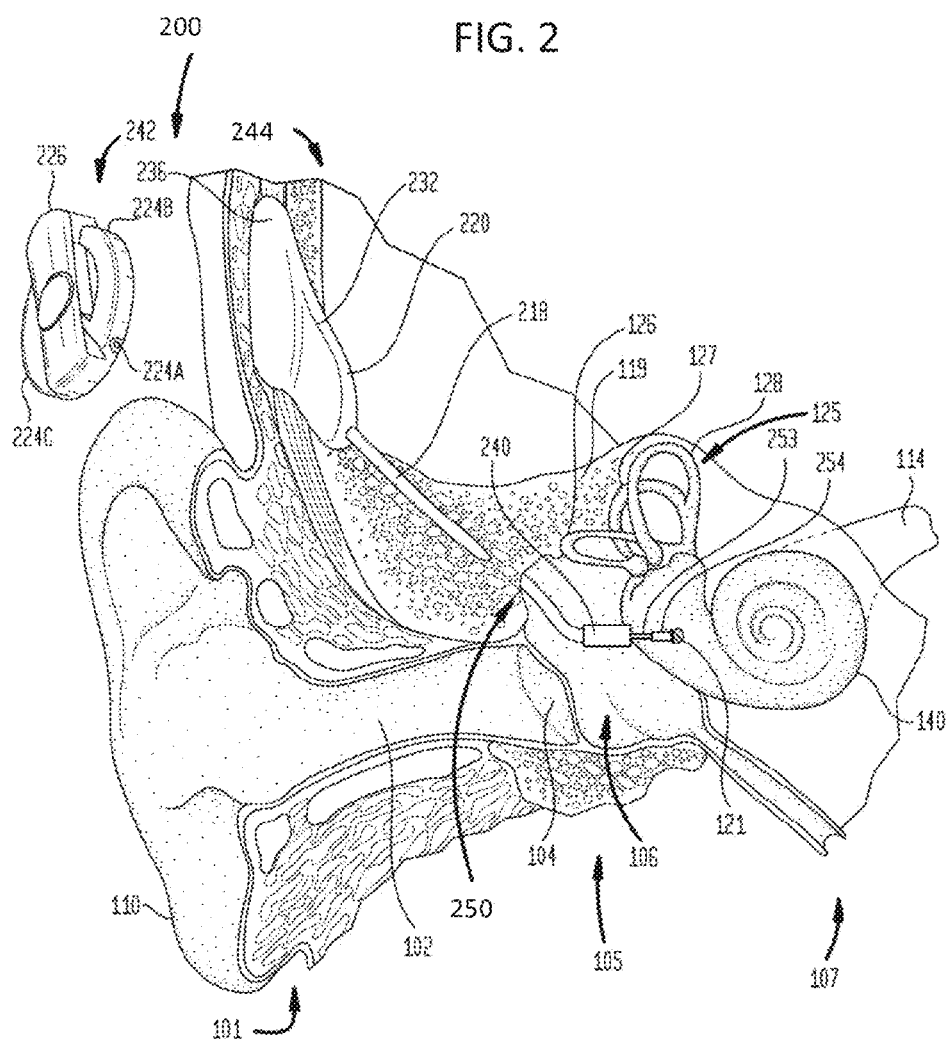
FIG. 2 is a perspective view of another exemplary hearing prosthesis utilized in some exemplary embodiments.

FIG. 2 is a perspective view of an exemplary direct acoustic cochlear implant (DACI) 200 in accordance with embodiments of the present invention. DACI 200 comprises an external component 242 that is directly or indirectly attached to the body of the recipient, and an internal component 244 that is temporarily or permanently implanted in the recipient. External component 242 typically comprises two or more sound input elements, such as microphones 224A, 224B, and 224C for detecting/capturing sound, a sound processing unit 226, a power source (not shown), and an external transmitter unit (also not shown). The external transmitter unit is disposed on the exterior surface of sound processing unit 226 and comprises an external coil (not shown). In an exemplary embodiment, external component 242 corresponds to a so-called "button sound processor" when it includes the sound processing unit 226. In an exemplary embodiment, external component 242 corresponds to a so-called "a button sound capture device" when it includes a microphone, whether it does or does not include a sound processing unit 226. Sound processing unit 226 processes the output of microphones 224 and generates encoded signals, sometimes referred to herein as encoded data signals, which are provided to the external transmitter unit. For ease of illustration, sound processing unit 226 is shown detached from the recipient.

In the present embodiment, microphones 224A, 224B, and 224C are configured as a microphone array, where sound processing unit 226 processes the signals received from the microphones 224A, 224B, and 224C to effect a microphone beam shape. For example, in an embodiment, the sound processing unit processes the signals received from microphones 224 to form microphone beam shape pointed towards the front of the recipient. A further description of exemplary beam shapes will be discussed below. Although microphones 224 are illustrated as dispersed around the edges of external component 242, in other embodiments the microphones 224 may be distributed in different configurations. For example, microphones 224 may be distributed on the outward facing face of external component 242. Additionally, in other embodiments the number of microphones 224 may be any number of two or more microphones that may be used for effecting a beam shape in particular direction.

Internal component 244 comprises an internal receiver unit 232, a stimulator unit 220, and a stimulation arrangement 250. Internal receiver unit 232 and stimulator unit 220 are hermetically sealed within a biocompatible housing, sometimes collectively referred to herein as a stimulator/receiver unit.

Internal receiver unit 232 comprises an internal coil (not shown), and preferably, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated single-strand/or multi-strand platinum or gold wire. The electrical insulation of the internal coil is provided by a flexible silicone molding (not shown). In use, implantable receiver unit 232 is positioned in a recess of the temporal bone adjacent auricle 110 of the recipient in the illustrated embodiment.

In the illustrative embodiment, stimulation arrangement 250 is implanted in middle ear 105. For ease of illustration, ossicles 106 have been omitted from FIG. 2. However, it should be appreciated that stimulation arrangement 250 is implanted without disturbing ossicles 106 in the illustrated embodiment.

Stimulation arrangement 250 comprises an actuator 240, a stapes prosthesis 254 and a coupling element 253 connecting the actuator to the stapes prosthesis. In this embodiment stimulation arrangement 250 is implanted and/or configured such that a portion of stapes prosthesis 254 abuts round window 121. In alternate embodiments, other coupling locations and coupling elements can be used. For example the actuator 240 can be coupled to the oval window, or alternatively, the actuator 240 may be coupled directly to one or more of the middle ear ossicles, etc.

As noted above, a sound signal is received by two or more microphones 224, processed by sound processing unit 226, and transmitted as encoded data signals to internal receiver 232. Based on these received signals, stimulator unit 220 generates drive signals which cause actuation of actuator 240. This actuation is transferred to stapes prosthesis 254 such that a wave of fluid motion is generated in the perilymph in scala tympani. Such fluid motion, in turn, activates the hair cells of the organ of Corti. Activation of the hair cells causes appropriate nerve impulses to be generated and transferred through the spiral ganglion cells (not shown) and auditory nerve 114 to the brain (also not shown) where they are perceived as sound.

It should be noted that the embodiments of FIGS. 1 and 2 are but two respective exemplary embodiments of a cochlear implant and a DACI, and in other embodiments other types of cochlear implants and/or DACIs are implanted. Further, although FIG. 2 provides illustrative examples of a direct acoustic cochlear stimulator system, in other embodiments a middle ear mechanical stimulation device can be configured in a similar manner, with the exception that instead of the actuator 240 being coupled to the inner ear of the recipient, the actuator is coupled to the middle ear of the recipient. For example, in an embodiment, the actuator stimulates the middle ear by direct mechanical coupling via coupling element to ossicles 106 (FIG. 1), such to incus 109 (FIG. 1).

Embodiments of the teachings detailed herein and/or variations thereof can be used with either (or both) of the respective hearing prostheses of FIGS. 1 and 2. Further, embodiments of the teachings detailed herein and/or variations thereof can be used with a combination of components from the aforementioned hearing prostheses (e.g., the cochlear implant 100 utilizing a button sound capture device or button sound processor 242, the DACI 200 with the BTE device 126 of FIG. 1, etc.). Further, embodiments of the teachings detailed herein and/or variations thereof can be used with other types of hearing prosthesis, such as by way of example only and not by way of limitation, bone conduction devices (e.g. percutaneous bone conduction devices, active transcutaneous bone conduction devices and/or passive transcutaneous bone conduction devices, variously including intra-oral bone conduction devices) and/or conventional acoustic hearing aids (e.g., in-the-ear (ITE) speakers). Also, embodiments the teachings detailed herein and/or variations thereof can be utilized as a stand-alone device, at least with respect to another hearing prosthesis.

Some exemplary embodiments will now be detailed with respect to the cochlear implant 100 detailed above. It is noted that in alternate embodiments, any of the aforementioned hearing prostheses can be substituted for the cochlear implant 100 described herein and/or combined with the cochlear implant 100. For example, teachings utilizing cochlear implant 100 also includes teachings utilizing a DACI, a bone conduction device, etc. For example, if feature X is taught in conjunction with cochlear implant 100, feature X is also taught in conjunction with DACI 200, feature X in conjunction with a bone conduction device, feature X in conjunction with an acoustic hearing aid, etc. It is noted at this time that the examples detailed herein are examples, and embodiments can differ from these examples. Any device, system or method, including various arrangements of systems that can be utilized to enable the teachings detailed herein and/or variations thereof can be used in some embodiments.

Figure 3A:
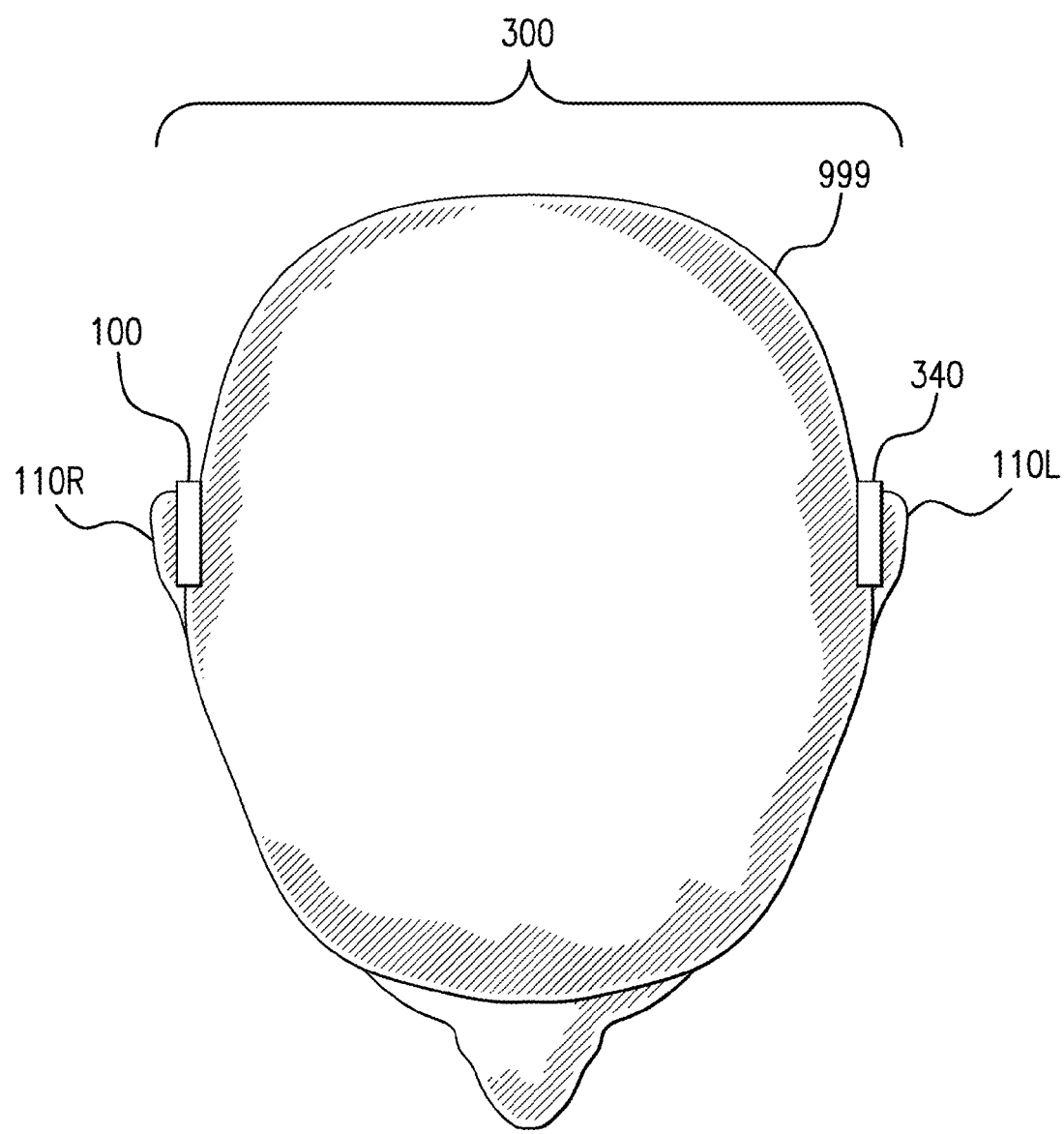
FIG. 3A is a high level functional diagram of an exemplary embodiment.

FIG. 3A depicts a high-level functional diagram of an exemplary system 300 applied to a recipient 999 (view is a top view—that is a view looking downward onto the recipient's head), with left and right auricle 110L and 110R, respectively. It is noted that the embodiment of FIG. 3A depicts one of many applications of the teachings detailed herein and/or variations thereof with respect to human physiology. In this regard, while the embodiment of FIG. 3A is depicted in terms of the utilization of two behind-the-ear devices, it is to be noted that in alternative embodiments, the teachings detailed herein and/or variations thereof can be implemented at other locations on the human body, as will be further described below.

System 300 includes a first prosthetic device 100 configured to evoke a hearing percept based on a first ambient sound, which, in the exemplary embodiment depicted in FIG. 3A, is the cochlear implant 100 of FIG. 1. System 300 also includes a second device 340. This second device is configured to stimulate skin based on a second captured sound, which may or may not be the same as the first captured sound, depending on the embodiment and/or the scenario of use. In an exemplary embodiment, device 340 is a non-invasive device, such as a BTE device (or a hand-held device—again, embodiments of system 300 are not limited to the human physiology depicted in FIG. 3A). Device 340 can stimulate the skin utilizing various principles of operations, such as by way of example only and not by way of limitation, vibratory energy, electrical energy, etc. In an exemplary embodiment, the second captured sound is sound generated by a voice of a speaker, such as, for example, the voice of a person speaking to the recipient. Additional exemplary details of the system 300 will now be described.

Figure 3B:
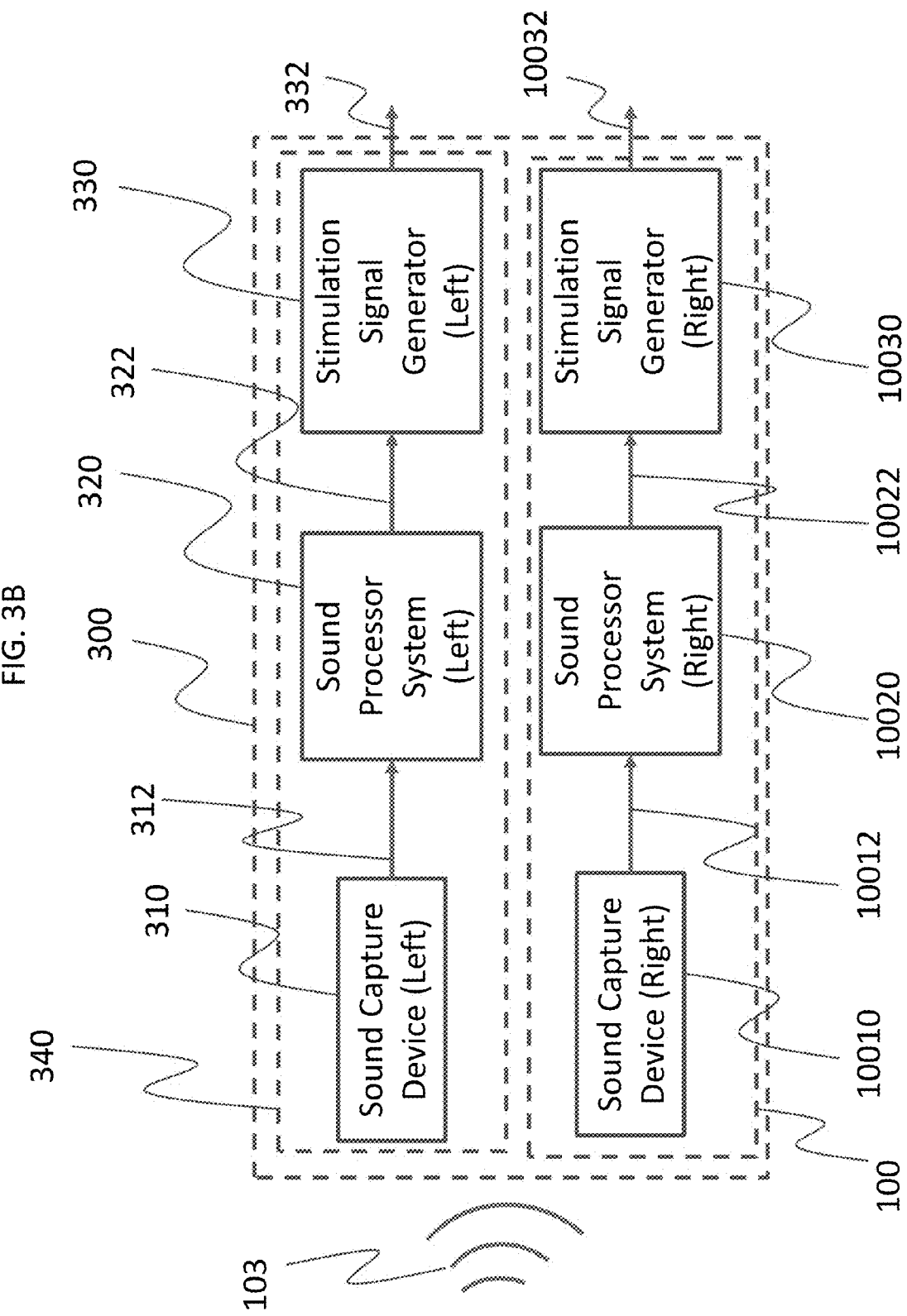
FIG. 3B is a medium level exemplary functional diagram of the exemplary embodiment of FIG. 3A.

FIG. 3B depicts a medium-level functional diagram of the exemplary system 300. System 300 includes subsystems 100 and 300, respectively corresponding to the cochlear implant 100 and the device 340 detailed above. The references to right and left refer to the sides of the recipient with respect to FIG. 3A (right side ear of the recipient 110R and left side ear of the recipient is 110L). In at least some embodiments detailed herein, each of these subsystems corresponds to a separate device that can operate independently of the other. For example, subsystem 100 can operate in the absence of subsystem 340, and vice-versa.

In an exemplary embodiment, subsystem 100 corresponds to the cochlear implant 100 detailed above with respect to FIG. 1. In an exemplary embodiment, subsystem 340 corresponds to a skin stimulator. It is noted that in some embodiments, the location of the sub-systems can be reversed (i.e., the subsystem 100 is on the left side and the subsystem 340 is on the right side).

Still referring to FIG. 3B, it can be seen that each subsystem includes a sound capture device (10010 and 310, respectively). In an exemplary embodiment, according to the description hereinafter, the sound capture devices can be microphones that can correspond to microphone 124 detailed above. In an alternate embodiment, one or both of the sound capture devices can instead be an audio jack that enables an audio signal to be inputted into the respective sub-system. Consistent with the embodiment of FIG. 3A which presents two separate devices that operate independently and separately from one another, each microphone 310 captures an ambient sound that originated acoustic pressure/soundwave 103 (which as noted above, would normally be collected by the auricles 110 (left and right side) of a person having normal hearing.

The captured ambient sound is converted by the microphones 10010 and 310 into audio signals 10012 and 312, respectively. These can be electrical signals, or can be optical signals or any other signal that enable communication between the microphones and their respective sound processors (10020 and 320, described below).

Upon receipt of the respective audio signals, the respective sound processors 10020 and 320 implement one or more sound coding/sound processing strategies to translate the respective audio signals into stimulation information signals. In an exemplary embodiment, sound processors 10020 and 320 can individually correspond to sound processing unit 126 detailed above, although the functionality can differ in one of them because such is utilized for skin stimulation as opposed to that used for the cochlear implant as detailed above. That said, in some embodiments, the functionality might be the same providing that the teachings detailed herein and/or variations thereof can be implemented.

Still referring to FIG. 3B, output information signals 10022 and 322 are respectively generated by the respective sound processor systems and are supplied to respective stimulation signal generators 10030 and 330. Accordingly, signals 10022 and 322 are control signals, as these signals are used to control the signal generators. In an exemplary embodiment, stimulating signal generator 10030 can correspond to stimulator unit 120 and electrodes 148 and accompanying components of cochlear implant 100, which, as noted above, generates stimulation signals which are applied by electrodes 148 to cochlea 140, thereby stimulating auditory nerve 114. In an exemplary embodiment, stimulating signal generator 330 can be a vibrator or an electrical stimulator unit coupled to electrodes in contact with the skin. The stimulation signal generators 10030 and 330 respectively output stimulation signals 10032 and 332. In an exemplary embodiment, when the sub-system 100 is a cochlear implant, signal 10032 is an electrical current. Further, when the sub-system 340 is a vibrator/includes a vibrator component, the signal 332 is vibrational energy. Alternatively or in addition to this, when sub-system 340 operates on a principle of operation of electrical stimulation of the skin, the signal 332 is electrical current. Accordingly, in an exemplary embodiment, when the sub-system 340 operates on both the principal operator operation of outputting vibrational energy and the principle of operation of outputting electrical current, there can be two signal generators and the output can be 332' and 332", respectively, where 332' is vibrational energy and 332" is electrical current. Hereinafter, reference to signal 332 corresponds to either or both of signals 332' and 332".

The sound processor system 320 can be configured such that the output thereof (signal 322) is based on frequencies indicative of a human voice (e.g., below 4 kHz, between about 500 Hz and about 4 kHz, etc.). For example, in the absence of frequencies below 4 kHz, sound processor system 320 does not output a signal and/or outputs a signal that instructs the stimulation signal generator 330 to not output signal 332. Alternatively and/or in addition to this, the sound processor system 320 can be configured to identify content of signal 312 indicative of a human voice, and output signal 322 based on content indicative of a human voice. Alternatively and/or in addition to this, the output of sound capture device 310 can be filtered or otherwise manipulated such that the signal that is provided to sound processor system 320 is based on frequencies and/or content indicative of a human voice. Alternatively, sound processor system 320 can utilize the envelope of the frequency of signal 312 to determine whether or not the signal is indicative of a human voice. Any device, system or method, that can enable sub-system 340 to evaluate whether a signal is indicative of a human voice, and thus provide skin simulation, can be used in at least some embodiments. In an alternate embodiment, the sound processor system can be configured such that the output thereof is based on the frequencies indicative of an animal voice, for example, a dog barking, etc. The system can be configured to provide skin stimulation when an animal voice is detected. An exemplary embodiment of such can have utilitarian value in that the skin stimulation can enhance the recipient's understanding of the context of the pet noise (e.g., angry growl, indicating that the recipient should back away; warning barking, indicating that the dog has detected a threat, etc.).

The sound processor system 320 can also be configured, in some other embodiments, such that the output thereof (signal 322) is based on frequencies that are detectable by the mechanoreceptors of the recipient for a given stimulation (e.g., vibrotactile stimulation and/or electrotactile stimulation, etc.). For example, the sound processor system 320 can utilize the envelope of the frequency of signal 312 to determine whether or not the signal is indicative of a signal that can evoke a detectable stimulation (i.e., detectible by the mechanoreceptors). Alternatively and/or in addition to this, the sound processor system 320 can utilize filtering to determine whether or not the signal is indicative of a signal that can evoke a detectable stimulation. The determination can be based on data pertaining to a specific recipient, and/or can be based on a statistical data relating to a sampling of a recipient population.

As noted above, the embodiment of FIG. 3B is configured such that both sub-systems thereof can operate independently of one another. In an alternative embodiment, now with reference to FIG. 3C, with like reference numbers corresponding to the elements of FIG. 3B, there is an exemplary system 3000 in which the sub-systems 100 and 340 interact with one another. In the embodiments of FIG. 3C, some components of the cochlear implant 100 are utilized to operate the stimulation signal generator 330 of the subsystem 340. This is done as a matter of exemplary convenience, and the opposite can be true in an alternative embodiment. Indeed, in an alternative embodiment, all of the components of FIG. 3B are present, and the components are configured to communicate with each other (e.g., the sound capture devices 10010 and 310 can output to the sound processor system 320 and 10020 respectively, in addition to outputting to the sound processor system 10020 and 320 respectively, as shown in FIG. 3B. Alternatively and/or in addition to this, the sound processor system 320 can output to the stimulation signal generator 10030, and the sound processor system 10020 can output to the stimulation signal generator 330, in addition to outputting to the stimulation signal generators as depicted in FIG. 3B.

Referring back to FIG. 3C, it can be seen that the sound processor system 10020 outputs a signal 10022 to the stimulation signal generator 10030, and also outputs a signal 322 to the stimulation signal generator 330, although in an alternate embodiment, it outputs the same signal (signal 10022) to stimulation signal generator 330. The sound processor system 10020 can be configured such that the signal 322 is based on frequencies indicative of a human voice (e.g., between about 500 Hz and about 4 kHz). For example, in the absence of frequencies below about 4 kHz and/or in the absence of frequencies between about 500 Hz and about 4 kHz, sound processor system 10020 does not output signal 322. Alternatively and/or in addition to this, the sound processor system 10020 can be configured to identify content of signal 10012 indicative of a human voice, and output signal 322 based on content indicative of a human voice. Meanwhile, sound processor system 10020 outputs a signal 10022, which can be based on the substantially full frequency spectrum (which includes the full frequency spectrum) and/or substantially the full content (which includes the full content) of the sound captured by the sound capture device 10010.

It is noted that system 300 and/or system 3000 can be configured such that the sub-systems 100 and 340 can communicate with each other. Indeed, in an exemplary embodiment of system 3000, such communication can enable the signal 322 (or other pertinent signal) generated by sub-system 100 to be sent to sub-system 340. In an exemplary embodiment, this communication is wireless, and is accomplished via, for example, radio frequency transmission and/or electromagnetic inductance, etc. In an alternate embodiment, the communication is via wire, which includes fiber optic cables etc. Any device, system and/or method that will enable sub-system 100 communicate with sub-system 340 can be utilized in at least some embodiments.

Thus, in some embodiments, the system 300 (and system 3000) and/or variations thereof evoke a hearing precept based on a first ambient sound, and stimulate skin based on a second ambient sound. In some embodiments, the second ambient sound is a subset of the first ambient sound (e.g., voice content stripped out or otherwise extracted from the overall ambient sound, where the ambient sound includes the voice content). Alternatively, in at least some embodiments of the systems detailed herein and/or variations thereof, the first and second ambient sounds can be the same. Both systems 300 and 3000 can do this in embodiments where the respective sound processor systems generate output signals based on the entire spectrum and/or contents of the sound captured by the sound capture devices.

Again, it is noted that the embodiments of FIGS. 3B and/or 3C and/or the variations detailed herein are but exemplary. Any device, system, and/or method that can enable stimulation signal generator 330 to output a signal 332 based on sound generated by a voice of a human can be utilized in at least some embodiments.

As noted above, system 300 (and system 3000) and/or variations thereof, in some embodiments, evoke a hearing precept based on a first ambient sound, and stimulate skin based on a second ambient sound. Also as noted above, in at least some embodiments of the systems detailed herein and/or variations thereof, the first and second ambient sounds can be the same. Both systems 300 and 3000 can do this in embodiments where the respective sound processor systems generate output signals based on the entire spectrum and/or contents of the sound captured by the sound capture devices. Conversely, in some alternative embodiments, the second ambient sound is a subset of the first ambient sound.

It is noted at this time that the output of the stimulation signal generator 330 of device 340 is different from that which would be the case with respect to a bone conduction device, in embodiments where signal 332 corresponds to vibratory energy, and different from that which would be the case with respect to a cochlear implants, in embodiments where signal 332 corresponds to electrical current. Indeed, in an exemplary embodiment, the device 340 is configured to stimulate skin without evoking a hearing percept when the device 340 is attached to a recipient having at least a partially functioning cochlea. That said, in some embodiments, the teachings detailed herein and/or variations thereof can be utilized with a bone conduction device (e.g. sub-system 100 is a bone conduction device) that evokes a hearing percept and/or signal 332 is superimposed onto a signal of a bone conduction device. Such exemplary embodiments are described in further detail below.) Indeed, in some embodiments, there is a device which can be switched from a pure bone conduction device to a vibrotactile device, and visa-versa. With this in mind, some exemplary functionalities of the system 300 in general, and the device 340 in particular will now be described.

According to an exemplary embodiment, system 300 enables the relative improvement, which, in at least some embodiments, is a substantial improvement, of the ability of the hearing impaired recipients to understand speech relative to that which would be the case in the absence of device 340 (i.e., only cochlear implant 100 is present). (This also includes system 3000—hereinafter, in the interest of textual economy, reference to system 300 and/or device 340 or any other system or device for that matter constitutes reference to any system and/or device applicable to system 3000/device 340 detailed herein and/or variations thereof unless otherwise specifically stated). In this regard, device 340 is configured to provide, in some embodiments, "speech cues" via skin stimulation, whether those cues be as a result of vibrational energy and/or electrical current, and/or another principle of operation (e.g., generating air pressure waves that impinge upon the skin). Device 340 can enable this by, for example, facilitating/improving recognition (including substantial facilitation/improvement) of certain characteristics of speech, such as for example, rhythm, duration, accents, and/or sonority, by outputting a skin stimulation signal 332 based on captured sound that includes speech, again, at least relative to that which would be the case in the absence of device 340. With respect to the exemplary embodiments of the system 300, these "speech cues" are complementary to the hearing percept evoked by the cochlear implant. Additional details of embodiments along these lines are described further below.

In essence, in an exemplary embodiment, device 340 communicates sound in general, and speech in particular, through the skin of the recipient. It is noted at this time that "through the skin" also includes the scenario where the device 340 in general, and the stimulatory portion thereof in particular, is located in the mouth and/or in any other enabling orifice of the recipient and/or where the device 340 is implanted in skin of the recipient, akin to an implantable microphone in the hearing prostheses arts, including those microphones that are isolated from the bone of the recipient via a layer of skin, muscle or fat, etc.

At least some of the embodiments detailed herein and/or variations thereof operate on a principle of operation where mechanoreceptors in the human skin are stimulated and/or activated by the signal 332. In the case of mechanical vibrations/vibrational energy corresponding to the stimulation, this is sometimes referred to herein as vibrotacticle stimulation. Alternatively, and/or in addition to this, as noted above, at least some of the embodiments detailed herein and/or variations thereof apply electric current as signal 332. Thus, mechanoreceptors receptors in the human skin are stimulated and/or activated by electrical current in such embodiments.

The parameters of the skin stimulation can vary depending on where the stimulation is applied to the skin. In this regard, as noted above, embodiments can include various locations of skin stimulation application. The following is a discussion detailing exemplary locations of the applied skin stimulation, exemplary devices that enable application at such locations, along with exemplary parameters of that skin stimulation with respect to exemplary location and/or exemplary device.

Figure 4A:
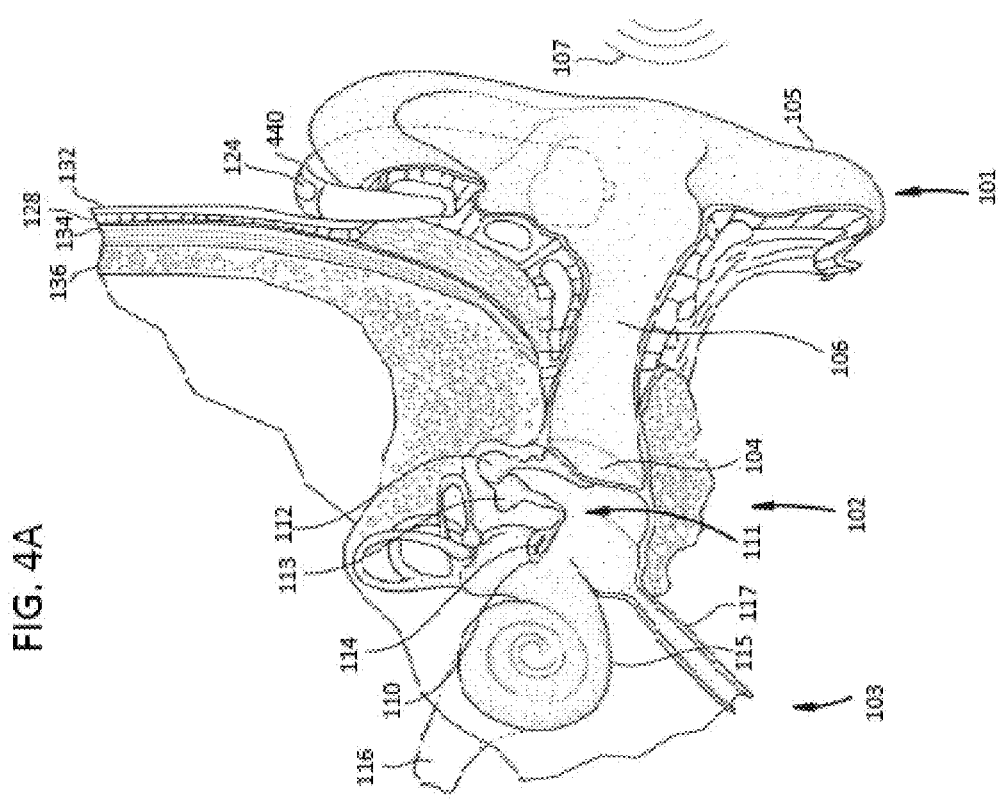
FIG. 4A is a perspective view of an exemplary device utilized in some exemplary embodiments.

Referring now to FIG. 4A, there is a device 440 in the form of a behind-the-ear device, corresponding to the device 340 described above in FIGS. 3A-3C. More particularly, FIG. 4A depicts portions of human physiology proximate to the left auricle 110L of FIG. 3A, where any of FIG. 1 or 2 depict portions of human physiology proximate to the right auricle 110R of FIG. 3A, the combination FIGS. 1 and 4A corresponding to system 300 (and the combination of FIGS. 2 and 4A corresponding to system 300 where sub-system 100 is a DACI). Behind-the-ear device 440 includes a vibrator device (not shown) corresponding to stimulation signal generator 330 of FIGS. 3B and/or 3C. In an exemplary embodiment, behind-the-ear device 440 corresponds to, in part and/or in whole, to the applicable teachings of U.S. patent application Ser. No. 13/596,477, filed on Aug. 28, 2012, albeit the functionality thereof can be different, although in other embodiments, the behind-the-ear device 440 corresponds to a different device.

Figure 4B:
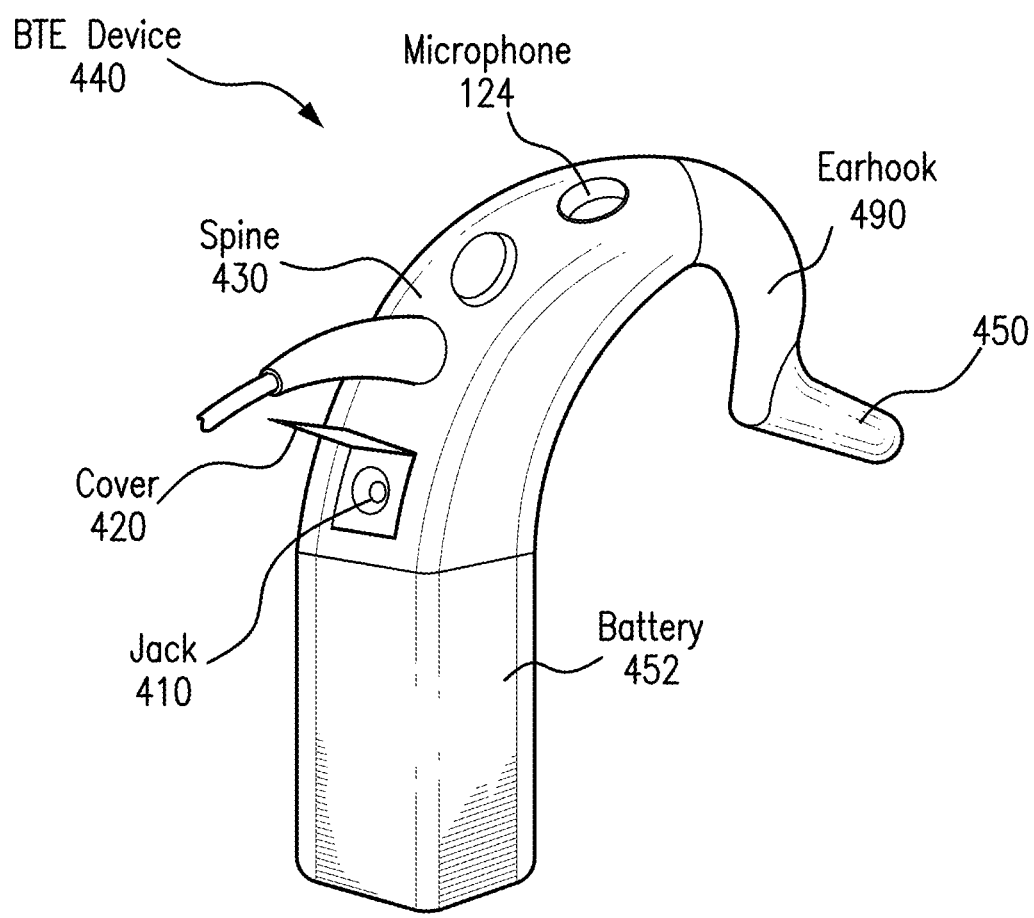
FIG. 4B is another perspective view of the exemplary device of FIG. 4A.

FIG. 4B is a rear perspective view of the BTE device 440. BTE device 440 includes one or more microphones 124, and may further include an audio signal jack 410 under a cover 420 on the spine 430 of BTE device 440. It is noted that in some other embodiments, one or both of these components (microphone 124 and/or jack 410) may be located on other positions of the BTE device 440, such as, for example, the side of the spine 230 (as opposed to the back of the spine 430, as depicted in FIG. 4B), the ear hook 490, etc. FIG. 4B further depicts battery 452 and ear hook 490 removably attached to spine 430.

BTE device 440 includes stimulator-skin interface 450 which extends from the end of ear hook 490, as can be seen in FIG. 4B. Stimulator-skin interface 450 is configured to abut or otherwise contact skin in front of the human auricle. In an exemplary embodiment, this contact is at a location at about between about the top, middle or bottom of the auricle and the closest eye of the recipient with respect to the surface of the recipient. In an exemplary embodiment, this contact is at a location at about between about the top, middle or bottom of the auricle and the portion of the mouth closest thereto of the recipient with respect to the surface of the recipient. In an exemplary embodiment, this contact is at a location at about between about the top, middle or bottom of the auricle and the closest nostril of the recipient with respect to the surface of the recipient.

While stimulator-skin interface 450 is depicted as a lobular extension of the earhook 490, in an alternative embodiment, the stimulator-skin interface 450 is an arm that extends from the end and/or middle portion of the ear hook 490. Any device, system, and/or method that will enable the stimulator-skin interface 450 to be located against the skin at a location that will enable utilitarian stimulation can be utilized in some embodiments.

In some embodiments, the geometry of the BTE device 440 in conjunction with the geometry of the human auricle is sufficient to result in utilitarian pressure on the skin of the recipient by the stimulator—skin interface 450. Alternatively and/or in addition to this, a portion of the BTE device 440 can be spring-loaded or otherwise be made of a resilient material that presses inward towards the skin, where the geometry of the BTE device 440 is sufficient to resist the reaction torque that results therefrom. In an exemplary embodiment, an adhesive can be utilized on the stimulator-skin interface surface that contacts the skin and/or around that surface. Any device, system and/or method that will enable the stimulator-skin interface to be held against the skin with sufficient force that will enable the teachings detailed herein and/or variations thereof to be practiced in a utilitarian manner can be utilized in at least some embodiments.

In an exemplary embodiment, the BTE device 440 includes a vibratory apparatus, and thus the device operates on a principle of operation of a vibrotactile stimulation/activation of the mechanoreceptors. In some embodiments, the vibratory apparatus is located in the stimulator-skin interface 450, while in other embodiments, the vibrator is located elsewhere, and a vibratory path is present in and/or on the BTE device 440 such that vibrations generated by the vibratory apparatus are transmitted along the path to the stimulator-skin interface 450.

In an alternate exemplary embodiment, the BTE device 440 includes an electrical stimulation generator, and thus the device operates on a principle of operation of electrotactile stimulation/activation of the mechanoreceptors. In some embodiments, the electrical stimulation generator is located in the stimulator-skin interface 450, while in other embodiments, the electrical stimulation generator is located elsewhere, and an electrical path is present in and/or on the BTE device 440 such that electrical current generated by the electrical stimulation generator are transmitted along the path to the stimulator-skin interface 450. In this regard, a surface of the stimulator-skin interface 450 includes one or more electrodes configured to electrically stimulate the skin.

In an alternate exemplary embodiment, the BTE device 440 includes both the vibratory apparatus and the electrical stimulation generator.

Figure 4C:
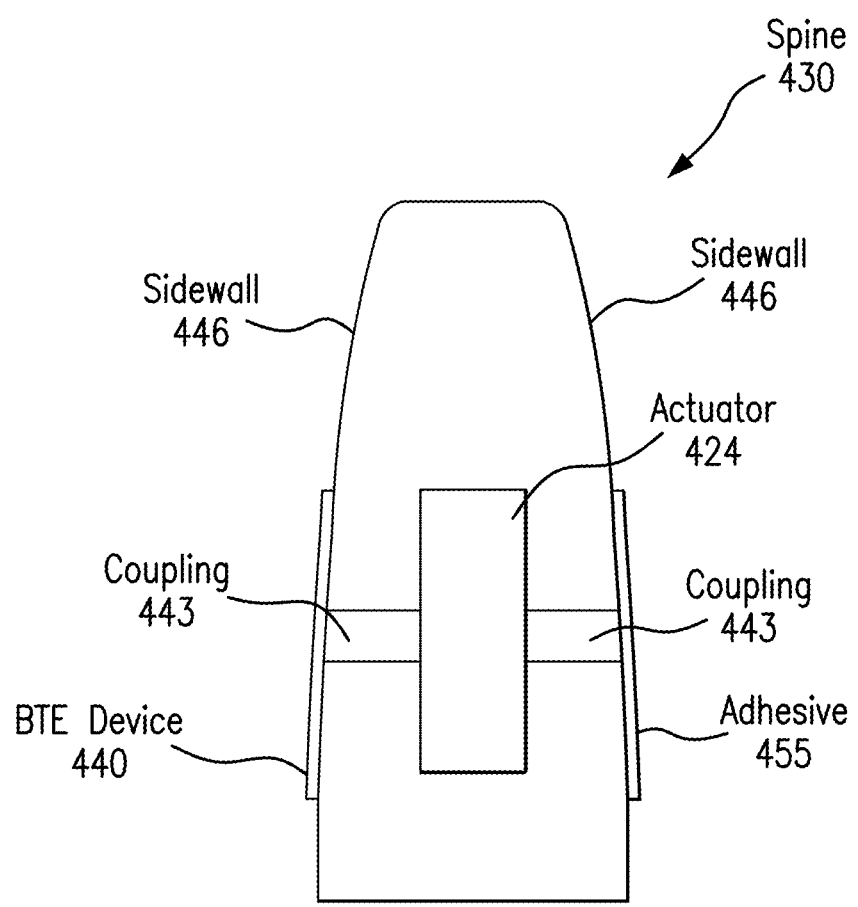
FIG. 4C is a rear view of a portion of the exemplary device of FIG. 4A.

It is noted that in other embodiments, the BTE device 440 is configured such that the vibrational stimulation and/or the electrical stimulation of the skin occurs behind the auricle of the recipient. Along these lines, FIG. 4C is a cross-sectional view of a spine 430 of BTE device 440 of FIG. 4B so configured. Actuator 442 is shown located within the spine 430 of BTE device 442. Actuator 442 is a vibratory apparatus with respect to vibrotactile embodiments, and is an electrical stimulation generator with respect to electrotactile embodiments. Actuator 442 is coupled to the sidewalls 446 of the spine 430 via couplings 443 which are configured to (i) transfer vibrations generated by actuator 442 to the sidewalls 446, from which those vibrations are transferred to skin 132, in the case of the vibrotactile embodiment, or (ii) transfer electrical current generated by actuator 442 to the sidewalls 446, from which those electrical currents are transferred to skin 132, in the case of the electrotactile embodiment. In some embodiments, the sidewalls 446 form at least part of a housing of spine 430. In some embodiments, the housing hermetically seals the interior of the spine 430 from the external environment.

Some exemplary features of the BTE device 440 of FIG. 4C will now be described. It is noted that in some embodiments, any one or more or all of the teachings detailed herein associated with the embodiment of FIG. 4C can be applicable to the embodiment of FIG. 4B and/or any other embodiments detailed herein and/or variations thereof.

FIG. 4C depicts adhesives 455 located on the sidewalls 446 of the BTE device 440. Adhesives 455 form coupling portions that are respectively configured to removably adhere the BTE device 440 to the recipient via adhesion at the locations of the adhesives 455. This adherence being in addition to that which might be provided by the presence of the earhook 490 and/or any grasping phenomenon resulting from the auricle 110 of the outer ear and the skin overlying the mastoid bone of the recipient.

It is noted that the embodiment of FIG. 4C is depicted with adhesives 455 located on both sides of the BTE device. In an exemplary embodiment of this embodiment, this permits the adherence properties detailed herein and/or variations thereof to be achieved regardless of whether the recipient wears the BTE device on the left side (in accordance with that depicted in FIG. 4A) or the left side (or wears two BTE devices). In an alternate embodiment, BTE device 440 includes adhesive only on one side (the side appropriate for the side on which the recipient intends to wear the BTE device 240). An embodiment of a BTE device includes a dual-side compatible BTE bone conduction device, as will be detailed below.

The adhesives 455 are depicted in FIG. 4C in an exaggerated manner so as to be more easily identified. In an exemplary embodiment, the adhesives 455 are double sided tape, where one side of the tape is protected by a barrier, such as a silicone paper, that is removed from the skin-side of the double-sided tape in relatively close temporal proximity to the placement of the BTE device 440 on the recipient. In an exemplary embodiment, adhesives 455 are glue or the like. In an exemplary embodiment where the adhesives 455 are glue, the glue may be applied in relatively close temporal proximity to the placement of the BTE device 440 on the recipient. Such application may be applied by the recipient to the spine 430, in an exemplary embodiment.

In an alternate embodiment, the adhesives 455 are of a configuration where the adhesive has relatively minimal adhesive properties during a temporal period when exposed to some conditions, and has relatively effective adhesive properties during a temporal period, such as a latter temporal period, when exposed to other conditions. Such a configuration can provide the recipient control over the adhesive properties of the adhesives.

By way of example, the glue and/or tape (double-sided or otherwise) may be a substance that obtains relatively effective adhesive properties when exposed to oil(s) and/or sweat produced by skin, when exposed to a certain amount of pressure, when exposed to body heat, etc., and/or a combination thereof and/or any other phenomena that may enable the teachings detailed herein and/or variations thereof to be practiced. Such exemplary phenomenon may be, for example, heat generated via friction resulting from the recipient rubbing his or her finger across the glue. In an exemplary embodiment, the pressure can be a pressure above that which may be expected to be experienced during normal handling of the spine 430.

In an exemplary embodiment, the adhesives 455 are contained in respective containers that exude glue or the like when exposed to certain conditions, such as by way of example and not by way of limitation, the aforementioned conditions. Alternatively and/or in addition to this, the recipient may puncture or otherwise open the containers to exude the glue or the like.

It is noted that in an exemplary embodiment, the teachings detailed herein and/or variations thereof associated with the adhesives can be utilized with any other device detailed herein and/or variations thereof. For example the adhesive 455 can be applied to element 450 of BTE device 440 of FIG. 4B to adhere the stimulator skin interface 450 to the skin of the recipient in front of the ear in the aforementioned locations.

Any device, system and/or method that will enable a recipient to practice the teachings detailed herein and/or variations thereof associated with the adherence of the stimulator-skin interface to skin of the recipient for stimulation transmission thereto can be utilized in some embodiments.

With respect to embodiments that utilize both electrotactile and vibrotactile stimulation of the mechanoreceptors, the stimulator-skin interface can be a single component and/or can be two separate components. For example an electrode surface can also be a surface from which vibrational energy is transferred. Still further, the electrode surface in combination with surrounding surface of the device can also be utilized to transfer vibrational energy. Conversely, one surface can be dedicated to vibrational energy transfer, and another service can be dedicated to electrical current transfer. Herein, unless otherwise specified, the stimulator-skin interface 450 can include any combinations thereof.

Another exemplary location where the stimulator-skin interface can be located is inside the ear canal. In an exemplary embodiment, device 340, in part and/or in whole, is an in-the-ear (ITE) device. In an exemplary embodiment, the stimulator-skin interface 450 is located on an outer surface of the ITE device that is contoured to the surface of the ear canal. In an exemplary embodiment, device 340, at least in embodiments where the entirety thereof corresponds to an ITE device, provides a "hidden" feature that improves cosmetics.

Figure 5:
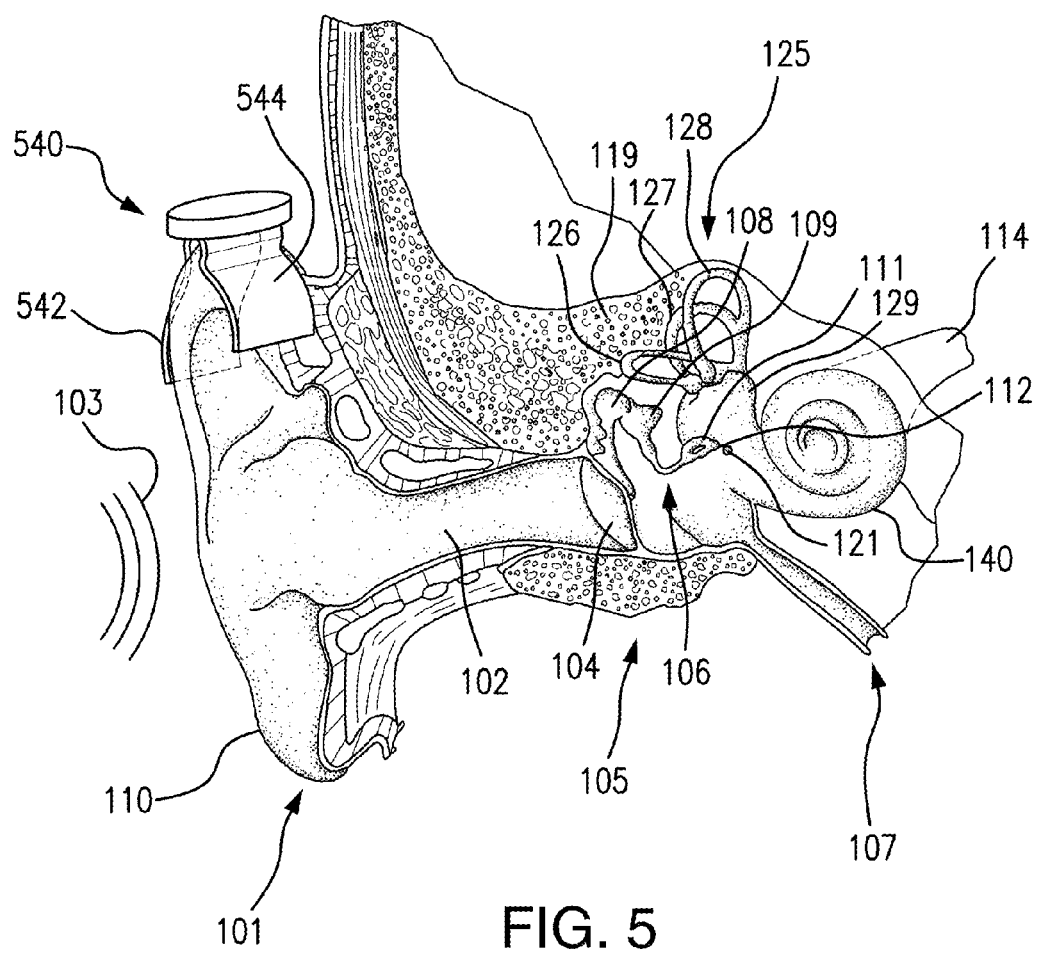
FIG. 5 is a view of another exemplary device utilized in some exemplary embodiments.

FIG. 5 presents yet another alternate embodiment of a device 540, corresponding to the device 340 of FIG. 3A. In this embodiment, device 540 clips, pinches or otherwise grips onto the auricle. The stimulator-skin interface of the device 540 is not shown, but it is located on the arm 542 of the device 540 and contacts the auricle on skin facing the skin of the skull covering the mastoid bone. In an alternative embodiment, both arms 542 and 544 include a stimulator-skin interface 450, which in some embodiments corresponds to respective dedicated vibrotactile and electrotactile stimulator-skin interfaces. In some embodiments, embodiments, one or both arms correspond to stimulator-skin interfaces that utilize one or both of the vibrotactile or electrotactile stimulation. In an exemplary embodiment, the device 540 is configured for vibrotactile and/or electrotactile stimulation/activation of the mechanoreceptors in the skin of the recipient. In alternate embodiments of the device 540, the clipping/gripping functionality of the device is utilized to only hold the device in place, and the stimulator-skin interface is located elsewhere. For example, instead of being positioned such that the stimulator-skin interface is located such that it contacts the auricle, instead it is located such that it contacts the skin over the mastoid bone behind and/or above and/or below the auricle. In an alternative embodiment, one or both of the arms of the device 540 that clips or otherwise grips onto the pinna includes a stimulator-skin interface, and in other stimulator-skin interface is located such that it contacts areas other than the pinna.

It is noted that while the embodiment of FIG. 5 depicts gripping on the top of the auricle, in an alternate embodiment, device 540 can grip the auricle at other locations, such as on the ear lobe or on the center of the auricle. Such exemplary locations can include a location that is at least about generally vertically aligned with the opening of the ear canal or above the ear canal but below the top of the auricle or below the ear canal but above the bottom of the ear lobe.

Figure 6:
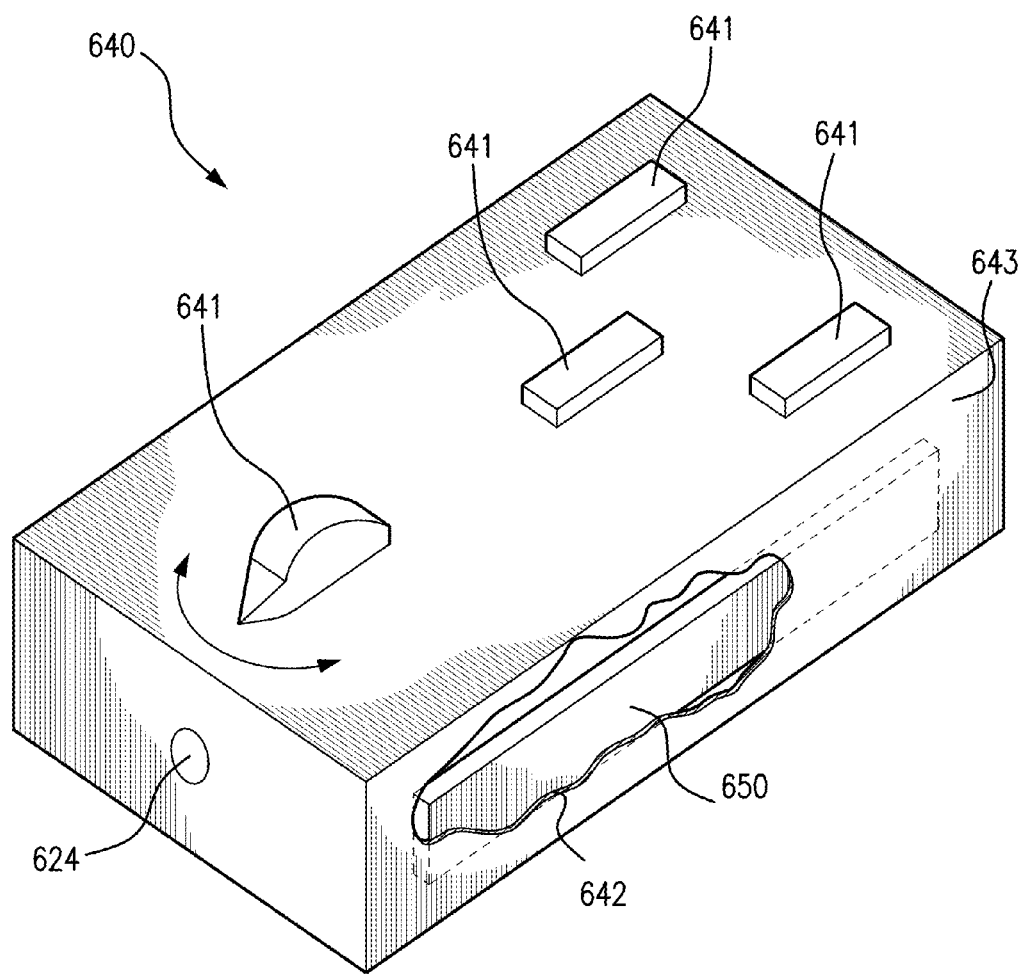
FIG. 6 is a view of another exemplary device utilized in some exemplary embodiments.

FIG. 6 depicts an alternate embodiment of a device corresponding to the functionality of device 340. Specifically, FIG. 6 depicts device 640, which is a hand-held electronic device in the form of a hand-held controller for cochlear implant 100. More specifically, hearing prostheses such as the cochlear implant 100, the DACI 200, etc., sometimes include a control device separate from the components that are implanted and attached or otherwise held against the recipient (e.g. the BTE device, a button sound processor, etc.). Such exemplary control devices can enable the adjustment of adjustable settings on these hearing prostheses. Device 640 is a conceptual example of a hand-held electronic device that communicates with cochlear implant 100 via a wireless link between device 640 and BTE device 126, although in alternate embodiments the link can be via wire, etc. Device 640 is configured to be held in the hand of a recipient, and enable the recipient to adjust settings of the cochlear implant 100 via input devices 641.

FIG. 6 depicts a cutaway section of side 643 of device 640, showing actuator 642 having a stimulator-skin interface 650 thereof. Side wall 643 is configured to be contacted by the fingertips of the recipient and/or by the mid-portions of the fingers of the recipient when the device 640 is held in a recipient's right-hand and the rotary dial is located closest to the thumb position of the hand. If device 640 is held in the recipient's left-hand, with the rotary dial likewise closest to the thumb, side wall 643 is configured to be contacted by the portion of the palm of the hand that constitutes the base of the thumb. Not shown in device 640 is the side opposite side wall 643. In an exemplary embodiment, that side also includes an actuator 642, although in an alternate embodiment, the actuator 642 extends from one side to the other side of the device 640, while in yet another alternate embodiment, a conductive path extends from the actuator to a stimulator-skin interface on the other side of the device. In such exemplary embodiments, this generally enables an actuator 642 (or, more specifically, a stimulator-skin interface) to be proximate the fingertips of the recipient (and, corollary to this, the base of the thumb) regardless of which hand the recipient holds the device 640, and/or regardless of the orientation with which the device 640 is held, at least with respect to the binary options of holding the device along its longitudinal axis. Accordingly, in an exemplary embodiment, the skin stimulation resulting from the use of device 640 enters the fingertips and/or enters the palm of the recipient's hand in general and into the base of the thumb in particular.

Actuator 642 is configured to output one or more signals 332 (332' and/or 332") based on, for example, sound captured by the sound capture device 10010 of the cochlear implant 100, and can be a vibrotactile stimulator and/or can be a electrotactile stimulator. In this regard, device 640 corresponds to the system 3000 of FIG. 3C. Actuator 642 is mounted on the side wall 643 of the device 640. In the embodiment depicted in FIG. 6, the actuator 642 extends through the side wall 643, and thus the stimulator-skin interface 650 of device 640 is the actuator 642. In an alternative embodiment, actuator 642 is mounted away from the outside surface of the side wall 643, and a conductive path from the actuator 642 leads to a stimulator-skin interface on the side of the device 640. In yet another alternate embodiment, there are one or more stimulator-skin interfaces and other locations of the device 640, such as by way of example and not by way of limitation, on the bottom surface, on the front surface, and/or on the back surface. These additional stimulator-skin interfaces may have dedicated actuators, and/or may share another actuator.

In an alternative embodiment, device 640 corresponds to the system 300 of FIG. 3B, where the device 640 operates independently of the cochlear implant 100. In an exemplary embodiment, device 640 includes a sound capture device 624, which in an exemplary embodiment, corresponds to a microphone. Device 640 further can include a sound processor system that receives signals from the microphone 624 and converts the signals into a signal 322 that is supplied to the actuators 642 so that the signal 332 is based on the sound captured by the microphone 624. Thus, in such an embodiment, vibrotactile stimulation and/or electrotactile stimulation based on an ambient sound can be provided to the recipient without reliance on the operation of the cochlear implant 100 and/or other associated hearing prostheses while still providing a controller to control the cochlear implant 100 and/or other associated hearing prostheses.

The functionality and/or principles of operations of the actuator 642 and the stimulator-skin interfaces 650 of the device 640 can correspond to those detailed herein with respect to other devices that have at least some of the functionality of device 340, and thus will not be repeated here.

Figure 7:
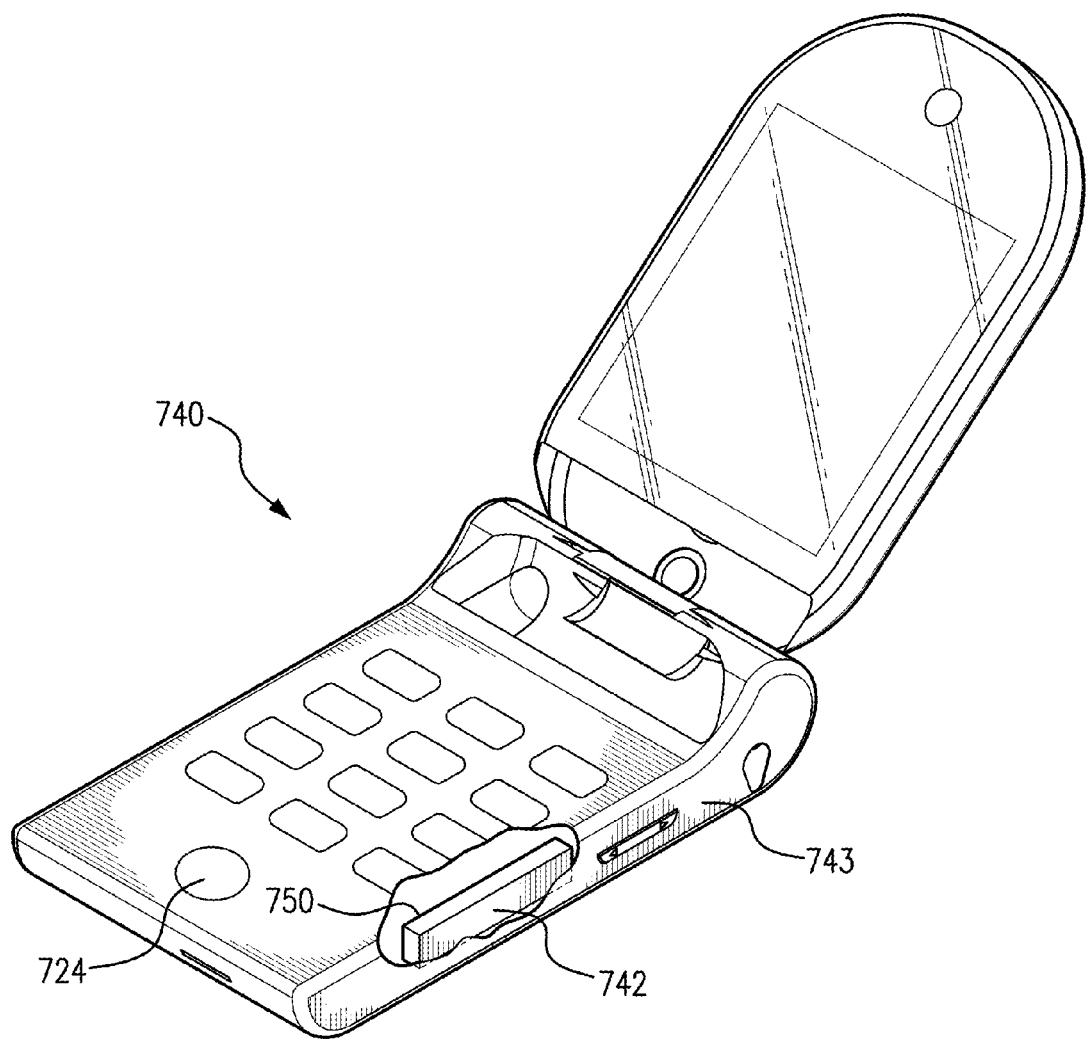
FIG. 7 is a view of another exemplary device utilized in some exemplary embodiments.

FIG. 7 depicts an alternate embodiment of a device corresponding to the functionality of device 340. Specifically, FIG. 7 depicts device 740, which is a hand-held electronic device in the form of a cellular phone. Device 740 is a conceptual example of a hand-held electronic device that can, in some embodiments, operate independently from and otherwise does not communicate with cochlear implant 100 (or other hearing prosthesis used by the recipient), thus corresponding to sub-system 340 of system 300 of FIG. 3B. However, in alternate embodiments, device 740 operates in conjunction with the cochlear implant 100 (or other hearing prosthesis used by the recipient), and, in some embodiments, communicates with the hearing prosthesis via a wireless link between device 740 and BTE device 126, although in alternate embodiments the link can be via wire, etc. Device 740 is configured to be held in the hand of a recipient.

FIG. 7 depicts a cutaway section of side 743 and a top portion of device 740, showing actuator 742 having a stimulator-skin interface 750 thereof. Side wall 743 is configured to be contacted by the fingertips of the recipient and/or by the mid-portions of the fingers of the recipient when the device 740 is held in a recipient's left-hand and the display is located closest to the thumb position of the hand. If device 740 is held in the recipient's right hand, with the display closest to the thumb, side 743 is configured to be contacted by the portion of the palm of the hand that constitutes the base of the thumb. Not shown in device 740 is the side opposite side wall 743. In an exemplary embodiment, that side also includes an actuator 742, although in an alternate embodiment, the actuator 742 extends from one side to the other side of the device 740, while in yet another alternate embodiment, a conductive path extends from the actuator to a stimulator-skin interface on the other side of the device. In such exemplary embodiments, this generally enables an actuator 742 (or, more specifically, a stimulator-skin interface) to be proximate the fingertips of the recipient (and, corollary to this, the base of the thumb) regardless of which hand the recipient holds the device 640, and/or regardless of the orientation with which the device 740 is held, at least with respect to the binary options of holding the device along its longitudinal axis. Accordingly, in an exemplary embodiment, the skin stimulation resulting from the use of device 740 enters the fingertips and/or enters the palm of the recipient's hand in general and into the base of the thumb in particular.

Actuator 742 is configured to output one or more signals 332 (332' and/or 332") based on, for example, sound captured by the sound capture device 10010 of the cochlear implant 100, and can be a vibrotactile stimulator and/or can be a electrotactile stimulator. In this regard, device 740 corresponds to the system 3000 of FIG. 3C. In an exemplary embodiment, the cochlear implant 100 communicates with device 740 via cellular communication or RF communication between the two devices so that the sound captured by the sound capture device 10010 and/or the signals outputted by the sound processor system 10020 can be transferred to the device 740. Actuator 742 is mounted on the side wall 743 of the device 740. In the embodiment depicted in FIG. 7, the actuator 742 extends through the side wall 743, and thus the stimulator-skin interface 750 of device 740 is the actuator 742. In an alternative embodiment, actuator 742 is mounted away from the outside surface of the side wall 743, and a conductive path from the actuator 742 leads to a stimulator-skin interface on the side of the device 740. In yet another alternate embodiment, there are one or more stimulator-skin interfaces and other locations of the device 740, such as by way of example and not by way of limitation, on the bottom surface, on the front surface, and/or on the back surface. These additional stimulator-skin interfaces may have dedicated actuators, and/or may share another actuator.

In an alternative embodiment, device 740 corresponds to the system 300 of FIG. 3B, where the device 740 operates independently of the cochlear implant 100 (or whatever hearing prosthesis might be utilized by the user of the device 740, if one is present at all). In an exemplary embodiment, device 740 includes a sound capture device 724, which in an exemplary embodiment, corresponds to a microphone, and, in some embodiments corresponds to the microphone of the cell phone that is used to capture the sounds of the users voice that are to be wirelessly transmitted to a listener of the user's voice. Device 740 further can include a sound processor system that receives signals from the microphone 724 and converts the signals into a signal 322, which, in some embodiments, is the signal that is used to be transmitted via the wireless connection between the cell phone and the cell phone tower in communication therewith, that is supplied to the actuators 742 so that the signal 332 is based on the sound captured by the microphone 724. Thus, in such an embodiment, vibrotactile stimulation and/or electrotactile stimulation based on an ambient sound can be provided to the recipient without reliance on the operation of the cochlear implant 100 and/or other associated hearing prosthesis. Indeed, in an exemplary embodiment, the user holds the cell phone in his or her hands, and allows the microphone 724 to capture the ambient sound, such as the sound of a speaker speaking to the user, this sound being the basis upon which the stimulation signal 332 is generated.

Figure 8:
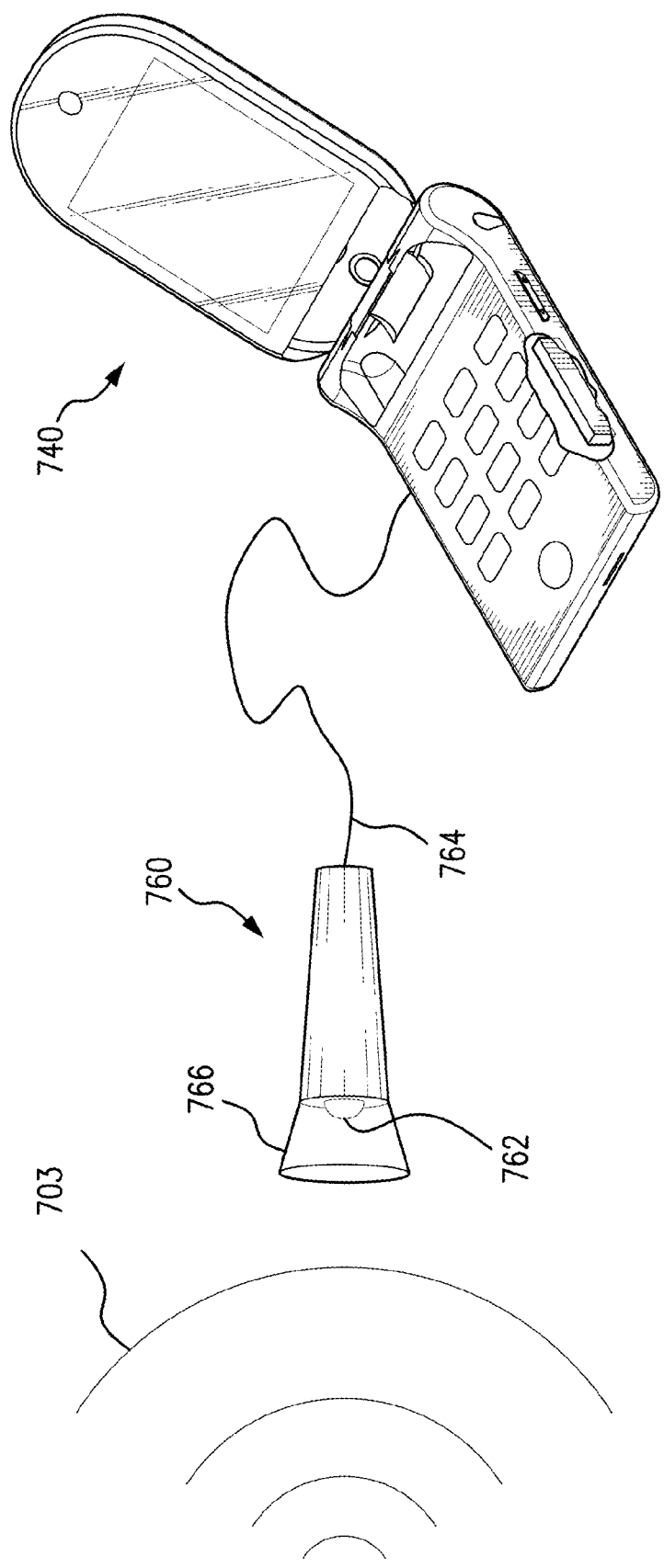
FIG. 8 is a view of another exemplary device utilized in some exemplary embodiments.

In an exemplary embodiment, a remote microphone can be connected to the device 740 and/or can otherwise be placed into communication with the sound processor of the device 740. In an exemplary method, the recipient holds the device 740 in one hand, and holds the remote microphone and another hand such that the remote microphone is closer to the speaker than the device 740. In an exemplary embodiment, the remote microphone has beamforming capabilities and/or is configured with a directionality feature such that the microphone is more sensitive or otherwise is more responsive to the speaker's voice than two other ambient sounds. In this regard, FIG. 8 depicts an exemplary embodiment of a remote microphone system 760 that is configured to be removably attached to and/or all turn at least placed into and out of communication with the device 740. The microphone system 760 includes a sound capture apparatus 762 that is configured to enable the recipient to direct or otherwise point the sound capture apparatus 762 towards a speaker's mouth that is producing sound waves 703 without moving the device 740. The microphone system 760 can include a cone shaped component 766 that funnels the pressure waves 703 to the sound capture apparatus 762. Alternatively and/or in addition to this, the microphone system 760 can include a beamforming feature that enables the recipient and/or enables the microphone system 760 to automatically capture the speech of the speaker/improve the content of speech captured by the speaker relative to that which would be the case in the absence of the feature.

The functionality and/or principles of operations of the actuator 742 and the stimulator-skin interfaces 750 of the device 740 can correspond to those detailed herein with respect to other devices that have at least some of the functionality of device 740, and thus will not be repeated here. That said, in an exemplary embodiment, the actuator 742 corresponds to the actuator that is present in the cell phone that produces the "vibrator mode" vibrations in "silent ringing mode" or "vibrate only" mode. In this regard, in an exemplary embodiment, actuator 742 corresponds to an eccentric rotating mass vibration motor (ERM), which is sometimes referred to as a "pager motor" or "pancake motor." By way of example, such devices can correspond to a DC motor with an offset (non-symmetrical) mass attached to a rotating shaft of the motor. In an exemplary embodiment, this is the vibrator that is utilized in cell phones. That said, in an alternate embodiment, a piezoelectric vibrator can also be used. Any device system and/or method that can utilize to provide vibrotactile (and/or electrotactile) stimulation to the skin can be utilized in some embodiments.

At least some exemplary embodiments, the actuators/vibrators that are utilized to evoke a vibrotactile stimulation output vibrations at frequencies of about 500 Hz or less, or at least the systems detailed herein and/or variations thereof output vibrational energy at the stimulator-skin interfaces at about 500 Hz or less. In an exemplary embodiment, there is an actuator/vibrator that is utilized in the system that vibrates at a frequency of and/or outputs vibrations at frequencies of and/or the vibrational energy output by the stimulator-skin interface is at a frequency of about and/or no greater than about 100, 150, 200, 250, 300, 350, 400, 450, 500, 550, 600 or about 650 Hz or more or any value or range of values therebetween in 1 Hz increments (e.g., about 357 Hz, about 455 Hz to about 600 Hz, etc.) or any frequency that can enable the teachings detailed herein and/or variations thereof to be utilized in a utilitarian manner in at least some embodiments. In an exemplary embodiment, the vibrator/actuators have resonant frequencies corresponding to and/or no greater than one or more of the aforementioned frequencies. In an exemplary embodiment, where the vibrator/actuator is an electromagnetic vibrator, output at such frequencies can have utilitarian value because efficiencies are increased, at least with respect to outputting vibrations at higher frequencies, such as by way of example one or two or three or four or more times any of the aforementioned frequencies.

As detailed above, some examples of device 340 can include two or more actuators, and thus can include two or more vibrators and/or two or more stimulator-skin interfaces. In an exemplary embodiment, these vibrators can have different resonant frequencies and/or can output vibrational energy at different frequencies and/or the respective stimulator-skin interfaces output vibrational energy at different frequencies, relative to one another. By way of example only and not by way of limitation, on the stimulator-skin interface outputs vibrational energies at 400 Hz, while another outputs vibrational energies at 500 Hz. In an exemplary embodiment, the device 340 is configured to (i) output vibrational energy from a first stimulator-skin interface at a frequency of about and/or no greater than about 100, 150, 200, 250, 300, 350, 400, 450, 500, 550, 600 or about 650 Hz or more or any value or range of values therebetween in 1 Hz increments (e.g., about 357 Hz, about 455 Hz to about 600 Hz, etc.) (ii) output vibrational energy from a second stimulator-skin interface at a frequency of about and/or no greater than about 100, 150, 200, 250, 300, 350, 400, 450, 500, 550, 600 or about 650 Hz or more or any value or range of values therebetween in 1 Hz increments (e.g., about 357 Hz, about 455 Hz to about 600 Hz, etc.) and/or (iii) output vibrational energy from a third stimulator-skin interface at a frequency of about and/or no greater than about 100, 150, 200, 250, 300, 350, 400, 450, 500, 550, 600 or about 650 Hz or more or any value or range of values therebetween in 1 Hz increments (e.g., about 357 Hz, about 455 Hz to about 600 Hz, etc.), etc.

In an exemplary embodiment, the system 300/3000 and/or other systems detailed herein and/or variations thereof is configured such that the magnitude of the output of the vibrational energy and/or the electrical energy that stimulates the skin is varied as a function of the frequency and/or amplitude of the component of the sound of interest (e.g., voice). For example, if the content of the sound corresponds to that of a relatively loud voice, the vibrational energy used to evoke a vibrotactile stimulation will have a relatively high magnitude (i.e., it will be relatively more forceful). Still further by example, if the content of the sound corresponds to that of a voice speaking with a normal loudness, the vibrational energy used to evoke a vibrotactile stimulation will have a moderate (uniform or consistent) magnitude (i.e., it will be at a level consistent with normal stimulation). Alternatively or in addition to this, if the content of the sound corresponds to that of a relatively loud voice, the vibrational energy used to evoke a vibrotactile stimulation will have a relatively high frequency or will have a relatively low frequency. A low frequency or a high frequency can be utilized depending on whether or not the recipient is more sensitive to such a frequency (more sensitive being utilitarian). Alternatively, the system could vary the frequency in a unique manner. All this as compared to the frequencies utilized if the content of the sound corresponds to that of a voice speaking with a normal loudness. In an exemplary embodiment, both amplitude and frequency can be varied accordingly.

Still further by example, if the content of the sound corresponds to that of a relatively loud voice, the electrical energy used to evoke an electrotactile stimulation will have a relatively high magnitude (i.e., it will be relatively more stimulating/shocking). Still further by example, if the content of the sound corresponds to that of a voice speaking with a normal loudness, the electrical energy used to evoke an electrotactile stimulation will have a moderate (uniform or consistent) magnitude (i.e., it will be at a level consistent with normal stimulation). Alternatively or in addition to this, if the content of the sound corresponds to that of a relatively loud voice, the electrical energy used to evoke an electrotactile stimulation will have a relatively high frequency or will have a relatively low frequency. A low frequency or a high frequency can be utilized depending on whether or not the recipient is more sensitive to such a frequency (more sensitive being utilitarian). Alternatively, the system could vary the frequency in a unique manner (e.g., radically varying the frequency from low to high to low, a steadily increasing frequency, a steadily decreasing frequency, etc.) All this as compared to the frequencies utilized if the content of the sound corresponds to that of a voice speaking with a normal loudness. In an exemplary embodiment, both amplitude and frequency can be varied accordingly.

In an exemplary embodiment, the system is configured to vary a pulse of the vibrational energy and/or the electrical energy. For example, the output for a loud voice could be the Morris code for SOS (or at least a portion thereof), or some other pattern that will have the attention of the recipient.

In still further embodiments, the system varies magnitude as a function of the frequency of the sound and/or the nature of the sound. For example, the system can relatively increase the magnitude for voice sounds or for certain voice sounds, and utilize a normal magnitude for other sounds, etc.

Along these lines, such embodiments can have utility in that for sounds representative of an urgent matter or the like (e.g., police siren, shouting, etc.), the system evokes a stronger stimulation/the stimulation attracts the attention of the recipient quicker/more forcefully. Such can enable the recipient to take notice of a particular noise and/or sound and/or voice in a manner that is faster or otherwise more likely than that which would otherwise be the case.

In an exemplary embodiment, the vibrators/stimulator-skin interfaces output high-energy at low frequencies. Any vibrator and/or vibrational frequencies that can be utilized to stimulate skin that can enable the teachings detailed herein and/or variations thereof to be practiced with utilitarian value can utilized in some embodiments.

It is also noted that in some embodiments, the vibrational energy that stimulates the skin can be applied in different manners. For example, in some embodiments, the vibrational energy is applied in a transverse manner to the skin. Conversely, in other embodiments, the vibrational energy is applied in a longitudinal manner to the skin. In some embodiments, a given device 340 outputs vibrational energy from one stimulator-skin interface in a transverse manner to the skin while outputting vibrational energy from another stimulator-skin interface in a longitudinal manner to the skin. In an exemplary embodiment, a single stimulator-skin interface can output vibrational energy in a transverse manner in some instances and output vibrational energy in a longitudinal manner in other instances, depending on the desired percept.

As noted above, at least some exemplary embodiments the teachings detailed herein and/or variations thereof are directed towards increasing speech understanding, including substantially increasing speech understanding utilizing skin stimulation, at least relative to that which would be the case in the absence of devices 340 (e.g. only utilizing a hearing prosthesis, such as by way of example, cochlear implant 100, DACI 200, a bone conduction device and/or an acoustic hearing aid). To this end, the devices 340 are configured to stimulate skin based on speech. In an exemplary embodiment, the system 300 (including system 3000) is configured to segregate or otherwise increase speech content from/relative to other ambient sounds (e.g. noise) such that the signals 332 are relatively substantially more based on speech content than that which would be the case in the absence of such segregation/increase. This can be done via a variety of sound processing techniques (e.g., band-pass/low-pass filtering, envelop filtering, etc.) and/or can be done via a beamforming and/or can be done via movement of the sound capture device relative to a speaker. This can also be done separately and/or in addition to this by advanced signal detection algorithms, which can isolate a speech signal from an audio signal. Any one or more or all of these systems/methods and/or other systems/methods that can achieve this feature can be utilized by the device 340/system 300 in at least some embodiments.

With regard to embodiments that utilize electrotactile stimulation, any device system and/or method that can enable the teachings detailed herein and/or variations thereof to be practiced can be utilized in some embodiments. In some exemplary embodiments, the voltage that is utilized to stimulate nerve fibers or to otherwise evoke a electrotactile stimulation they can be perceived by recipient in a utilitarian manner is between about 1 or 2 volts to about 9 hundred or 1000 volts. In an exemplary embodiment, where stimulation is applied to the fingers and/or to the abdomen, voltage can be about 30, about 40, about 50 to about 400, 500, or 600 volts. When stimulation is applied to, for example, the tongue, and/or the cheek, or other tissues within the mouth, voltages can be about 1, 2, 3, 4, 5 6, 7, 8, 9, 10, 11, 12, 13, 14, 15, 16, 17, 18, 19 or about 20 volts. Any voltage and current that can enable electrotactile stimulation to meet the teachings detailed herein and/or variations thereof can be utilized in at least some embodiments.

The embodiments detailed above generally focused on systems where the hearing prosthesis was an entirely separate device from the device that applies the skin stimulation, albeit in some embodiments there is communication between the two devices. In other embodiments, the hearing prosthesis itself is configured to apply skin stimulation. Some exemplary embodiments of such embodiments will now be described.

In an exemplary embodiment, there is a hearing prosthesis corresponding to cochlear implant 100, where the BTE device 126 includes an actuator configured to provide electrotactile stimulation and/or vibrotactile stimulation to skin of the recipient according to the teachings detailed herein and/or variations thereof. In this regard, with respect to the embodiments of FIG. 3C, system 3000 corresponds to sub-system 100, and sub-system 340 is a subsystem of the sub-system 100. That said, in some such embodiments, the sub-system 340 can still be a separate system, even though it is housed or otherwise contained in the components of cochlear implant 100. That is, element 100 of FIG. 1 corresponds to system 300 of FIG. 3B, and the components of the cochlear implant 100 correspond to a sub-system of the system. It is noted that a BTE device of a DACI, a bone conduction device, and/or an acoustic hearing aid can also be configured to provide vibrotactile stimulation and/or electrotactile stimulation to the skin. In a similar vein, there is a hearing prosthesis corresponding to DACI 200, where the button sound capture device 242, which, in some embodiments, is a button sound processor, includes an actuator configured to provide a vibrotactile stimulation and/or any electrotactile stimulation to the skin of the recipient according to the teachings detailed herein and/or variations thereof (e.g., the button sound capture device includes sub-system 340). It is noted that a button sound capture device of a cochlear implant, a bone conduction device, and/or an acoustic hearing aid can also be configured to provide vibrotactile stimulation and/or electrotactile stimulation to the skin.

In some exemplary embodiments in which the actuator is located in a button sound capture device and/or a BTE device, some and/or all of the features associated with the other devices that have the functionality of device 340 detailed herein and/or variations thereof are utilized with these embodiments. By way of example only and not by way of limitation, in the scenario where the actuator is located in the BTE device, adhesives as detailed respect to the embodiment of FIG. 4C can be utilized, even though such adhesive would not normally be utilized in the case of a traditional cochlear implants.

It is noted that at least some of the embodiments detailed herein include an actuator that provides the vibrotactile stimulation housed or otherwise supported in the same component that supports or otherwise contains the sound capture device (e.g. microphone). A scenario exists where feedback resulting from the vibrations from the actuator results in a deleterious signal processing regime relative to that which would be the case in the absence of such feedback. Accordingly, in some embodiments, the microphone and/or the actuator that generates the vibrational energy are vibrational isolated from one another. In an exemplary embodiment, the microphones are located in/supported by a separate component. For example, a microphone of a hearing prosthesis BTE device can be used to capture sound (e.g. speech), and the signals therefrom and/or signals based thereon, (e.g., signal resulting from the sound processor regime of the captured sound) can be transferred to another BTE device located on the opposite side of the recipient's head corresponding to device 340, with respect to the embodiments of FIG. 3C. Alternatively and/or in addition to this, device 340 can be bifurcated into include two separate components that are separate from each other, one supporting the microphone and the other supporting the vibrating actuator. For example, there can be a first device having some of the functionality of device 340, that device including BTE device that includes a sound capture device and, optionally a sound processor, but does not include an actuator, or at least not a vibrating actuator (it might conclude and electrotactile stimulation generator, etc.). There can further be a second device also having the some of the functionality of device 340, that can be in the form of an auricle clip akin to the embodiments of FIG. 5, and/or can include a handheld device corresponding to the embodiment of FIG. 6 and/or FIG. 7, or another handheld device that simply corresponds to a housing in which and/or on which an actuator is located, with or without a microphone and/or with or without sound processing componentry, but including an actuator configured to output vibrational energy to evoke a vibrotactile stimulation.

That said, in some embodiments, there are signal processing techniques and/or sound capture techniques that are utilized to reduce (which includes substantially eliminating (which includes eliminate)) feedback that might otherwise occur in the system, all things being equal. For example, embodiments can include a system such that the frequency band of the output of the sound capture device is filtered such that there is no frequency overlap with the output of the sound capture device and the frequency band of the skin stimulation (e.g., vibrational energy at 550 Hz resulting from speech within 600 Hz to about 4 kHz). Accordingly, in an exemplary embodiment, there is a system 300 (including system 3000) that is configured such that signal 332 is based on sound captured by a sound capture device having frequencies above the frequency of the signal 332, including substantially above the signal 332. Accordingly, in an exemplary embodiment where system 3000 corresponds to system where subsystem 100 is a cochlear implant or other type of hearing prosthesis, and subsystem 340 receives input based on a shared sound capture device (such as the sound capture device 10010 of the subsystem 100), and the output signal 332 is a signal having a frequency that is below (including substantially below) frequencies upon which sound processor system 10020 output signals to the stimulation signal generator 10030 to evoke a hearing percept, the likelihood of feedback, or at least significant feedback occurring resulting from signal 332 is effectively reduced (including substantially reduced) relative to that which would be the case if the sound processor system 10020 output signals to the stimulation signal generator 10030 to evoke a hearing percept at frequencies at or below that of signal 332. In such an exemplary embodiment, the microphone and/or the vibrating actuator can be relatively close to each other.

Figure 9:
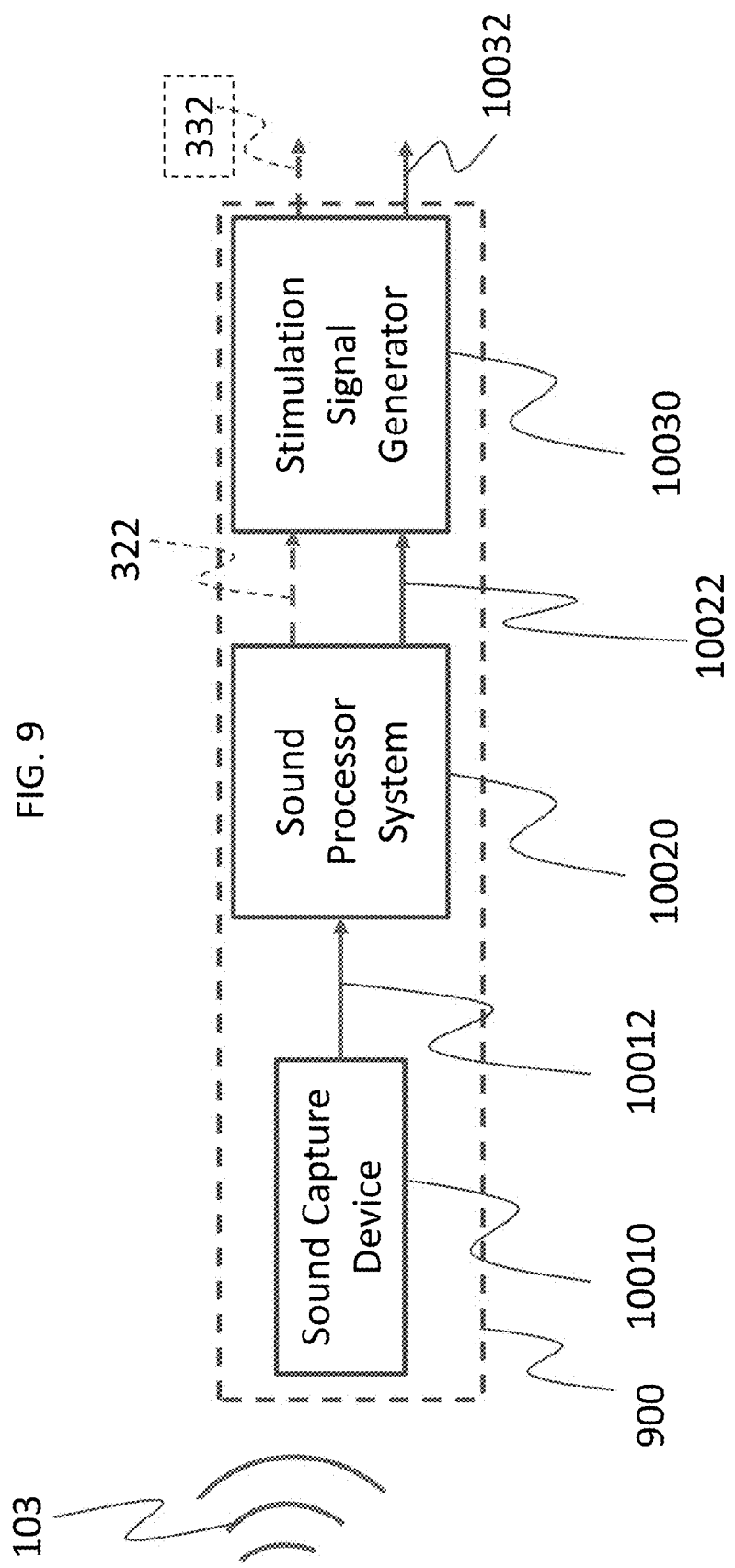
FIG. 9 is a medium level exemplary functional diagraph of an exemplary device utilized in some exemplary embodiments.

Referring now to FIG. 9, there is an exemplary functional block diagram of a bone conduction device 900, such as by way of example and not by way of limitation, a passive transcutaneous bone conduction device, according to an exemplary embodiment, with like reference numbers corresponding to the elements of FIG. 3B above. In the embodiment of FIG. 9, the sound processor system 10020 is configured to increase the gain of the output signal 10022 at low frequencies in a manner that increases the vibrotactile stimulation of the skin resulting from the signal 10032 output by the stimulation signal generator 10030, which in an exemplary embodiment is electromagnetic vibrator actuator and/or piezoelectric vibrator actuator. In an alternative embodiment, instead of and/or in addition to the sound processor system 10020 being configured to increase the gain of the output signal, filters and/or amplifiers are located upstream of the sound processor system 10020 at or after the sound capture device 10010 such that low frequency signals are amplified prior to being fixed to the sound processor system 10020.

In an alternate embodiment, still with reference to FIG. 9, output of the stimulation signal generator 10030 includes two components, a first, normal bone conduction component 10032, corresponding to vibrations configured to evoke a hearing percept, and a second component 332, corresponding to vibrations, such as vibrations at or below 650 Hz, configured to evoke vibrotactile stimulation of the skin according to the teachings detailed herein and/or variations thereof. In an exemplary embodiment, output 332 is overlaid onto output 10032.

In yet an alternate embodiment, the device of FIG. 9 and/or an alternate device is configured such that the device can variously operate in a bone conduction mode and a vibrotactile mode. In an exemplary embodiment, the device can operate in a bone conduction mode, a vibrotactile mode, and a bone conduction/vibrotactile mode (a combined mode). For example, device 900 (or an alternative device) is configured such that a user can control the device to be in one or more of the aforementioned modes. Alternatively and/or in addition to this, the device is configured such that it automatically enters one or more of the aforementioned modes. By way of example only and not by way of limitation, device 900 can include a switch or other type of control unit that enables the recipient to switch from the bone conduction mode to the vibrotactile mode and/or to the combined mode (if such a mode exists in that particular embodiment). An exemplary embodiment includes a control unit that enables such switching automatically. This enables the device to be utilized as a traditional bone conduction device and/or as a vibrotactile device according to the teachings detailed herein and/or variation thereof, depending on the desires of the recipient/user or depending on the circumstances. In at least some embodiments, the same vibrator is utilized in all of the aforementioned modes to obtain the respective stimulus. Accordingly, in an exemplary embodiment, there is a method of utilizing a device according to any of the teachings detailed herein and/or variations thereof and adjusting the mode of the device from a vibrotactile mode to a bone conduction mode and/or to a combination mode, and permutations and variations thereof. In an exemplary embodiment, the methods are executed such that the same vibrator (actuator) is used to obtain the vibrotactile stimulation and the bone conduction stimulation.

Figure 10:
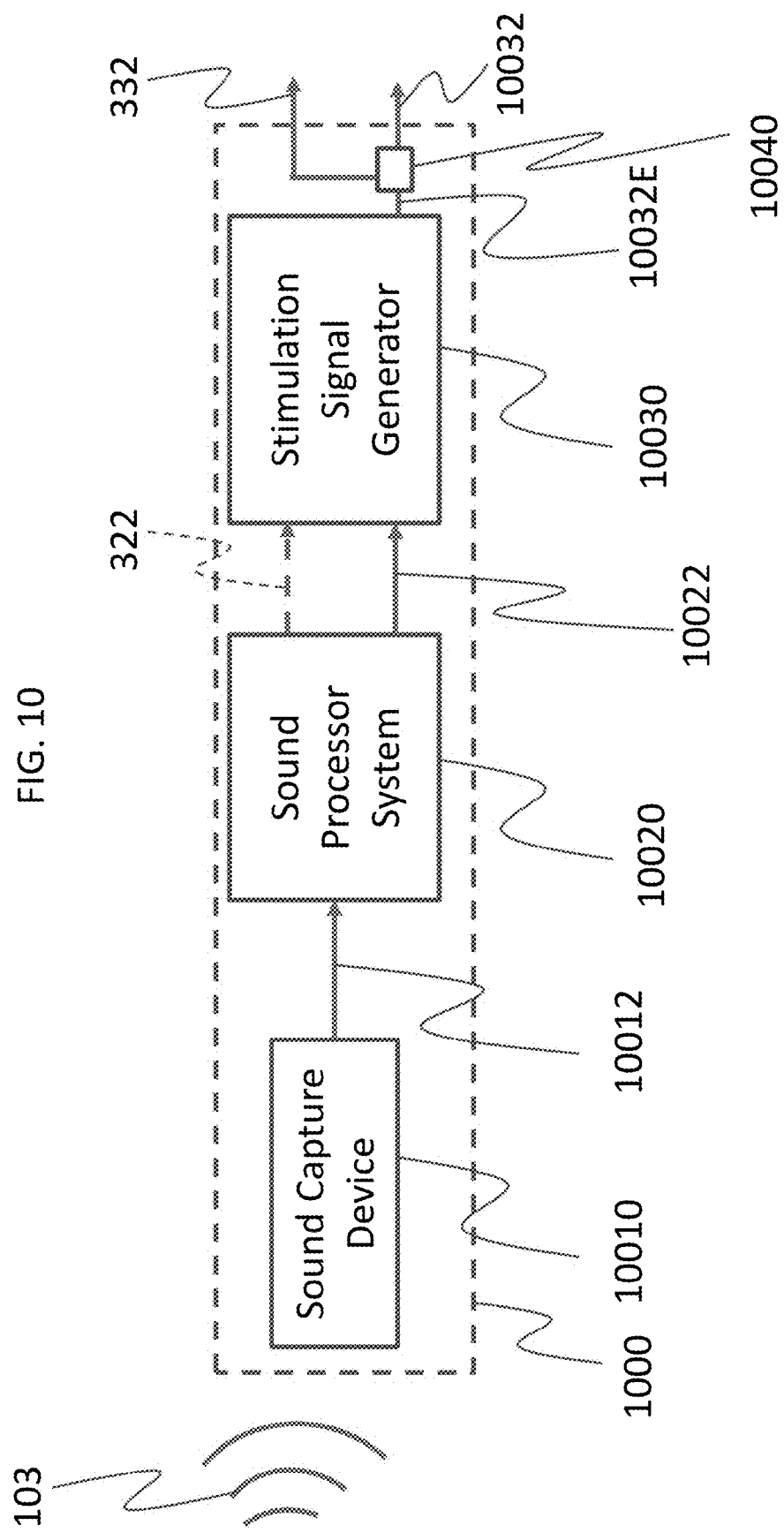
FIG. 10 is a medium level exemplary functional diagraph of another exemplary device utilized in some exemplary embodiments.

Now referring to the embodiment of FIG. 10 with like reference numbers of FIG. 9 corresponding to the respective components thereof, there is an alternate embodiment in which the bone conduction device 1000, where, in some embodiments, some and/or all of the features and/or functionalities detailed above with respect to bone conduction device 900 are included in bone conduction device 1000. In bone conduction device 1000, the stimulation signal generator is configured to output a quasi-embryonic signal 10032E, which corresponds to signal 10032 with respect to the embodiment of FIG. 9. This signal is outputted to a component of the bone conduction device 1000 (not illustrated) that is positioned against the skin of the recipient. In an exemplary embodiment, this component corresponds to a vibration plate or the like of an external component of a passive transcutaneous bone conduction device. Bone conduction device 1000 further includes unit 10040, which varies a geometric feature of that component of the bone conduction device, such as by way of example only and not by way of limitation, the contact area of that component. By varying the geometric feature of that contact component, the output of the bone conduction device 1000 can include a normal operating component 10032 and a skin stimulation component 332, at least relative to a baseline geometric feature. As with all of the embodiments detailed herein and/or variations thereof, signal 332 can be a signal that evokes a skin stimulation but does not evoke a hearing percept, or at least does not evoke an effective hearing percept.

Alternatively and/or in addition to this, unit 10040 can be a unit that receives signal 10032E, which corresponds to normal output of a stimulation signal generator (e.g. electromagnetic transducer) of a bone conduction device, and generates an electrical current in the form of signal 332 based on that received signal 10032E, and allows signal 10032E to pass to the recipient in the form of signal 10032, to evoke a hearing percept via bone conduction. Accordingly in an exemplary embodiment, there is a method of retrofitting a bone conduction device, such as a passive transcutaneous bone conduction device that is initially only configured to output vibrational energy, into a device that outputs both vibrational energy and an electric current, the latter being utilized to evoke an electrotactile stimulation of the skin. It is noted that while unit 10040 is depicted as being downstream of the stimulation signal generator 10032, in alternate embodiments, 10040 can be located upstream of the site stimulation signal generator.

In an exemplary embodiment, there is an exemplary bone conduction device configured such that a recipient can place the bone conduction device into a skin stimulation mode from a hearing percept mode, and visa-versa. For example, the bone conduction device is limited to outputting vibrations at frequencies of no more than the frequencies detailed herein with respect to vibrotactile stimulation at energy levels that do not evoke a hearing percept when in the skin stimulation mode. The bone conduction device is not so limited when in the hearing percept mode (instead, it outputs vibrations at frequencies up to 5 kHz, 7 kHz, 9 kHz, 10 kHz, 12 kHz, 15 kHz, or more).

In an exemplary embodiment, there is an exemplary method utilizing system 300 in a bilateral deaf person, where sub-system 100 corresponds to a cochlear implant, a DACI, etc., and the microphone for such sub-system 100 is located on one side of the recent, and the microphone for sub-system 340 is located on the other side of the recipient. In such an exemplary method, the head shadow effect, which relates to the acoustic shadow due to the sound being obstructed by the head, associated with the hearing prosthesis of sub-system 100, is effectively reduced, including substantially reduced relative to that which would be the case in the absence of sub-system 340.

Some exemplary utilities of at least some of the teachings detailed herein and/or variations thereof will now be described. It is noted at this time that with respect to the methods and/or functions of components described herein, embodiments include any device and/or system that can enable or otherwise allow for those methods (in total and/or with respect to any individual actions or group of actions of those methods) to be practiced and/or for that functionality to be achieved. Conversely, with respect to the variety of apparatuses and systems disclosed herein, embodiments include any method of utilizing those apparatuses and/or systems, etc.

In an exemplary embodiment, there is an exemplary method of utilizing system 300 to achieve cross modal plasticity in the auditory system of a human having a hearing defect (e.g. deafness in one and/or both ears). For example, there is a method of utilizing system 300 over a period of time such that the vibrotactile and/or electrotactile stimulation obtained through utilization of device 340 in conjunction with the hearing prostheses associated therewith (e.g. cochlear implant 100) results in at least a partial rerouting of the sense of touch to the auditory parts of the recipient, such as the auditory parts of the brain. In such an exemplary method, at least in some embodiments, the use of the hearing prosthesis to evoke a hearing percept combined with the use of device 340, which in at least some embodiments does not result in the application of a hearing percept, provides a correlation between the hearing percept evoked by the hearing prostheses and the stimulation of the skin that results in the aforementioned cross modal plasticity. In such an exemplary method, at least in some embodiments, the combined use of the hearing prosthesis to evoke a hearing percept with the use of the device 340 (i.e., system 300), which in at least some embodiments does not result in the application of a hearing percept, results in cross modal plasticity. In an exemplary embodiment, this cross modal plasticity is such that after a period of time using system 300 (e.g., about 100, 150, 200, 250, 300, 500, 600, 1000, 1500 or about 2000 hours or more or any value or range of values therebetween in about 10 hour increments or any period of time that will enable the teachings detailed herein to be practiced), the recipient who is hearing impaired (e.g. totally deaf), can understand words spoken to him or her at a certain level, without looking at the speaker and without utilizing the hearing prosthesis, effectively greater than that which would be the case in the absence of device 340 and the absence of the hearing prosthesis and without looking at the speaker. Indeed, with respect to the example where the recipient is totally deaf, any ability whatsoever to make out or otherwise perceive or understand spoken words without utilizing a hearing prosthesis and without looking at the speaker's lips amounts to understanding words at a level that is effectively greater than that which would otherwise be the case.

In an exemplary embodiment, this cross modal plasticity is such that after a period of time using system 300 according to any of those detailed herein and/or alternative time periods that will enable the teachings detailed herein to be practiced, the recipient can understand words spoken to him or her at a level, without utilizing the hearing prosthesis but while looking at the speaker's lips, effectively greater than that which would be the case in the absence of device 340 and the absence of the hearing prosthesis but while looking at the speaker's lips.

In an exemplary embodiment, the levels that are effectively greater can correspond to, for example, the ability to understand about 5, 10, 15, 20, 25, 30, 35, 40, 45, 50% or more words or any value or range of values therebetween in 1% increments, than that which would be the case in the alternative. In an exemplary embodiment, implementing one or more of the methods detailed herein and/or variations thereof can result in the ability to correctly identify words through so-called speech reading to be improved with respect to phonemes that share the same viseme by about 5, 10, 15, 20, 25, 30, 35, 40, 45, 50% or more words or any value or range of values therebetween in 1% increments, relative to that which would be the case in the alternative (i.e., not implementing one or more of the methods detailed herein). In an exemplary embodiment, implementing one or more of the methods detailed herein and/or variations thereof can result in the ability to correctly identify words through so-called speech reading to be improved with respect to words that cannot be distinguished based on site alone (i.e., lip reading) by about 5, 10, 15, 20, 25, 30, 35, 40, 45, 50% or more words or any value or range of values therebetween in 1% increments, relative to that which would be the case in the alternative (i.e., not implementing one or more of the methods detailed herein). The aforementioned examples can be for a totally deaf person.

Some embodiments include methods of mapping speech phonemes against different frequencies and/or different stimulation locations, and utilizing system 300 and/or executing one or more the methods detailed herein and/or variations thereof based on such mapping. In an exemplary embodiment, there is a method that entails stimulating skin utilizing a first group of frequencies and/or at a first group of locations (including one frequency and/or on location) on a recipient for a first group of phonemes, and stimulating skin utilizing a second group of frequencies and/or at a second group of locations (including one frequency and/or on location) on a recipient for a second group of phonemes, The first group of frequencies and/or the first group of locations are different than the second group of frequencies and/or the second group of locations (although specific locations and/or frequencies within the groups may be present in both groups). The first group of phonemes are different than the second group of phonemes (although certain phonemes within the group may be present in both groups). These methods can be practices in conjunction with a hearing prosthesis or without such hearing prosthesis.

It is noted that in some embodiments, the methods, devices and systems detailed herein and/or variations thereof enable a wide recognition of phonemes while in other embodiments, the methods device and systems detailed herein and/or variations thereof enable a more limited recognition of phonems. With regard to the latter, there are a number of scenarios where only limited recognition provides utilitarian value. It is further noted that some embodiments of the skin stimulation detailed herein and/or variations thereof result in a conscious percept by the recipient of the stimulation, while in other embodiments, the skin stimulation results in a subconscious percept by the recipient of the stimulation. In an exemplary embodiment, the latter can have utility in the case of cross modal plasticity. Still further, the latter can have utility with respect to the improved identification of phonemes or the like, to the extent that subconscious percept can enable the recognition of the phonemes. Any amounts of stimulation in any manner that can enable the teachings detailed herein and/or variations thereof can be utilized in at least some embodiments.

In view of the above, there is a method comprising evoking a hearing percept in a recipient based on a first captured sound. The method further includes the action of simultaneously stimulating skin of the recipient based on a second captured sound, wherein the stimulation of the skin does not evoke a hearing percept. As detailed herein, the first captured sound in the second captured sound can be the same captured sound, while in other embodiments that the captured sounds can be different. In at least some exemplary methods, the skin stimulation evokes a phoneme recognition level effectively beyond that which would be the case in the absence of the skin stimulation. In an exemplary embodiment, the recognition level is 5, 10, 15, 20, 25, 30, 35, 40, 45, 50% or more or any value or range of values therebetween in 1% increments greater than that which would be the case in the absence of skin stimulation.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A system, comprising:
a first prosthetic device configured to evoke a hearing percept based on a first ambient sound; and
a second non-invasive device configured to stimulate skin based on a second ambient sound generated by a voice, wherein
the first device is a cochlear implant, and
at least one of:
(i) the second device is a vibrator; or
(ii) the cochlear implant is configured to electrically stimulate a cochlea of a recipient;
and
the second device is an electrical stimulator configured to electrically stimulate skin of a recipient.

2. The system of claim 1, wherein:
the second device is configured to stimulate skin without evoking a hearing percept when attached to a recipient of the system having at least a partially functioning cochlea.

3. The system of claim 1, wherein:
the second ambient sound is the same as the first ambient sound.

4. The system of claim 1, wherein:
the second ambient sound is a subset of the first ambient sound.

5. The system of claim 1, wherein:
the second device is the vibrator.

6. The system of claim 1, wherein:
the cochlear implant is configured to electrically stimulate the cochlea of the recipient; and
the second device is the electrical stimulator configured to electrically stimulate skin of the recipient.

7. The system of claim 1, wherein:
the second device is a behind-the-ear device.

8. The system of claim 1, wherein:
the second device is a vibrator having a resonant frequency no greater than about 600 Hz.

9. The system of claim 1, wherein:
the second device is a vibrator having a resonant frequency no greater than about 550 Hz.

10. The system of claim 1, wherein:
the second device is a vibrator having a resonant frequency no greater than about 500 Hz.

11. The system of claim 1, wherein:
the second device includes a plurality of vibrators having different resonant frequencies.

12. The system of claim 1, wherein:
the second device is a button sound capture device configured to wirelessly communicate with the first prosthetic device.

13. The system of claim 1, wherein:
the second non-invasive device is configured to stimulate the skin via delivery of skin stimulation in the form of vibrational energy at only a single frequency.

14. A system, comprising:
a hearing prosthesis configured to evoke a hearing percept based on a first captured sound;
a hand-held electronic device in communication with the hearing prosthesis, wherein the hand-held electronic device is configured to stimulate skin based on the first captured sound, wherein
the hand-held electronic device includes a vibrational apparatus configured to deliver the skin stimulation in the form of vibrational energy at only a single frequency.

15. The system of claim 14, wherein:
the hand-held electronic device has a hearing prosthesis control functionality.

16. The system of claim 14, wherein:
the hearing prosthesis is a cochlear implant; and
the vibrational apparatus of the hand-held electronic device includes a vibrator.

17. The system of claim 14, wherein:
the vibrational apparatus has a resonant frequency no greater than about 600 Hz.

18. A method, comprising:
evoking a hearing percept in a recipient based on a first ambient sound; and
simultaneously evoking a tactile percept in the recipient based on a second ambient sound, wherein the evoked tactile percept does not evoke a hearing percept.

19. The method of claim 18, wherein:
the first ambient sound and the second ambient sound are the same sound.

20. The method of claim 18, wherein:
wherein the tactical percept corresponds to delivery of skin stimulation in the form of vibrational energy at only a single frequency.

21. The method of claim 18, wherein:
the recipient has at least a partially functioning cochlea.

22. The method of claim 18, wherein:
a device that is attached to skin of the recipient is utilized to evoke the tactile percept.

* * * * *